US009895451B2

(12) United States Patent
Saltzman et al.

(10) Patent No.: US 9,895,451 B2
(45) Date of Patent: *Feb. 20, 2018

(54) FORMULATIONS FOR TARGETED RELEASE OF AGENTS TO LOW PH TISSUE ENVIRONMENTS OR CELLULAR COMPARTMENTS AND METHODS OF USE THEREOF

(71) Applicant: Yale University, New Haven, CT (US)

(72) Inventors: W. Mark Saltzman, New Haven, CT (US); Junwei Zhang, New Haven, CT (US); Jiangbing Zhou, Cheshire, CT (US); Zhaozhong Jiang, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/547,051

(22) Filed: Nov. 18, 2014

(65) Prior Publication Data

US 2015/0073041 A1 Mar. 12, 2015

Related U.S. Application Data

(63) Continuation-in-part of application No. 14/293,733, filed on Jun. 2, 2014, now Pat. No. 9,272,043, and a continuation-in-part of application No. PCT/US2012/067447, filed on Nov. 30, 2012.

(60) Provisional application No. 61/870,497, filed on Aug. 27, 2013, provisional application No. 61/566,412, filed on Dec. 2, 2011.

(51) Int. Cl.
| | |
|---|---|
| *A61K 47/48* | (2006.01) |
| *A61K 47/59* | (2017.01) |
| *A61K 31/7088* | (2006.01) |
| *A61K 9/51* | (2006.01) |
| *C08G 63/685* | (2006.01) |
| *A61K 47/34* | (2017.01) |
| *A61K 9/107* | (2006.01) |
| *C12N 15/87* | (2006.01) |

(52) U.S. Cl.
CPC .......... *A61K 47/593* (2017.08); *A61K 9/5146* (2013.01); *A61K 31/7088* (2013.01); *C08G 63/685* (2013.01); *A61K 9/1075* (2013.01); *A61K 47/34* (2013.01); *C12N 15/87* (2013.01)

(58) Field of Classification Search
CPC .. A61K 31/7088; A61K 47/34; A61K 47/482; A61K 9/1075; A61K 9/5146; A61K 47/48; C08G 63/685; C12N 15/87
USPC .......... 435/459; 514/44 A; 528/291
See application file for complete search history.

(56) References Cited

U.S. PATENT DOCUMENTS

| | | | |
|---|---|---|---|
| 5,034,506 A | 7/1991 | Summerton | |
| 5,142,047 A | 8/1992 | Summerton | |
| 5,166,315 A | 11/1992 | Summerton | |
| 5,217,866 A | 6/1993 | Summerton | |
| 5,506,337 A | 4/1996 | Summerton | |
| 5,521,063 A | 5/1996 | Summerton | |
| 5,527,675 A | 6/1996 | Coull | |
| 5,539,082 A | 7/1996 | Nielsen | |
| 5,623,049 A | 4/1997 | Lobberding | |
| 5,698,546 A | 12/1997 | Bridger | |
| 5,698,685 A | 12/1997 | Summerton | |
| 5,714,331 A | 2/1998 | Buchardt | |
| 5,736,336 A | 4/1998 | Buchardt | |
| 5,773,571 A | 6/1998 | Nielsen | |
| 5,786,571 A | 7/1998 | Bethel | |
| 9,272,043 B2 * | 3/2016 | Saltzman | A61K 47/34 |
| 2007/0219122 A1 | 9/2007 | Glazer | |
| 2008/0050920 A1 | 2/2008 | Kawahara | |
| 2011/0008451 A1 | 1/2011 | Saltzman | |
| 2011/0262406 A1 | 10/2011 | delCampo | |

FOREIGN PATENT DOCUMENTS

| | | |
|---|---|---|
| WO | 1993012096 | 6/1993 |
| WO | 2002010142 | 2/2002 |

OTHER PUBLICATIONS

Al-Dosari, et al., "Nonviral gene delivery: principle, limitations, and recent progress", AAPS J.,11:671-81 (2009).
Braasch, et al., "Locked nucleic acid (LNA): fine-tuning the recognition of DNA and RNA", Chem. Biol., 8(1):1-7 (2001).
Chen, et al., "Targeted nanoparticles deliver siRNA to melanoma", J. Invest. Dermatol., 130: 2790-8 (2010).
Davanloo, et al., "Cloning and expression of the gene for bacteriophage T7 RNA polymerase", PNAS, 81:2035-39 (1984).
Felgner, et al., "Enhanced gene delivery and mechanism studies with a novel series of cationic lipid formulations", J. Biol. Chem., 269:2550-61 (1994).
Felgner, et al., "Lipofection: a highly efficient, lipid-mediated DNA-transfection procedure", PNAS, 84:7413-7 (1987).

(Continued)

*Primary Examiner* — Janet L Epps-Smith

(74) *Attorney, Agent, or Firm* — Pabst Patent Group LLP

(57) ABSTRACT

Polyamine-co-ester-co-ortho ester) polymers, methods of forming active agent-load nanoparticles therefrom, and methods of using the nanoparticles for drug delivery are disclosed. The nanoparticles can be coated with an agent that reduces surface charge, an agent that increases cell-specific targeting, or a combination thereof. Typically, the loaded nanoparticles are less toxic, more efficient at drug delivery, or a combination thereof compared to a control or other transfection reagents.

28 Claims, 5 Drawing Sheets

(56) References Cited

OTHER PUBLICATIONS

Gao, et al., Nonviral gene delivery: what we know and what is next AAPS J., 9:E92-E104 (2007).
Gao, et al., "The association of autophagy with polyethylenimine-induced cytotoxicity in nephritic and hepatic cell lines", Biomaterials, 32:8613-25 (2011).
Harris, et al., "Tissue-specific gene delivery via nanoparticle coating", Biomaterials, 31:998-1006 (2010).
Hu, et al., "Reaction parameters of targeted gene repair in mammalian cells", Mol. Biotech., 29:197-210 (2005).
Jiang, "Lipase-catalyzed synthesis of poly(amine-co-esters) via copolymerization of diester with amino-substituted diol", Biomacromolecules,11:1089-93 (2010).
Kafil, et al., "Cytotoxic impacts of linear and branched polyethylenimine nanostructures in a431 cells", BioImpacts, 1:23-30 (2011).
Liu, et al., "Hydrodynamics-based transfection in animals by systemic administration of plasmid DNA", Gene Ther., 6:1258-66 (1999).
Liu, et al., "Enzyme-synthesized poly(amine-co-esters) as nonviral vectors for gene delivery", J. Biomed. Mater. Res., 96A:456-65 (2011).
Lv, et al., "Toxicity of cationic lipids and cationic polymers in gene delivery", J Contr. Rel., 114:100-9 (2006).
Martinez, et al., "Single-stranded antisense siRNAs guide target RNA cleavage in RNAi", Cell, 110:563-74 (2002).
Nagayama, et al., "Time-dependent changes in opsonin amount associated on nanoparticles alter their hepatic uptake characteristics", Int. J. Pharm., 342:215-21 (2007).
Nicol, et al., "Poly-L-glutamate, an anionic polymer, enhances transgene expression for plasmids delivered by intramuscular injection with in vivo electroporation", Gene. Ther., 9:1351-8 (2002).
Nykanen, et al., "ATP requirements and small interfering RNA structure in the RNA interference pathway", Cell, 107:309-21 (2001).
Olsen, et al., "Genomic sequence correction by single-stranded DNA oligonucleotides: role of DNA synthesis and chemical modifications of the oligonucleotide ends", J. Gene Med., 7:1534-44 (2005).
Schlegel, et al., "Anionic polymers for decreased toxicity and enhanced in vivo delivery of siRNA complexed with cationic liposomes", J. Contr. Rel., 152:393-401 (2011).
Sterchak, et al., "Uncharged stereoregular nucleic acid analogs. 1. Synthesis of a cytosine-containing oligomer with carbamate internucleoside linkages", Organic Chem., 52:4202, (1987).
Templeton, et al, "Improved DNA: liposome complexes for increased systemic delivery and gene expression", Nat. Biotechnol., 15:647-52 (1997).
Tros De Ilarduya, et al., "Gene delivery by lipoplexes and polyplexes", Eur. J. Pharm. Sci., 40:159-70 (2010).
Wang, et al., "Synthesis and characterization of cationic micelles self-assembled from a biodegradable copolymer for gene delivery", Biomacromolecules, 8:1028-37 (2007).
Wang, et al., "The self-assembly of biodegradable cationic polymer micelles as vectors for gene transfection", Biomaterials, 28:5358-68 (2007b).
Weising, et al.,"Foreign genes in plants: transfer, structure, expression, and applications", Ann. Rev. Genetics, 22:421 (1988).
Zhang, et al., "Galactosylated ternary DNA/polyphosphoramidate nanoparticles mediate high gene transfection efficiency in hepatocytes", J. Controlled Release, 102:749-63 (2005).

* cited by examiner

FORMULATIONS FOR TARGETED RELEASE OF AGENTS TO LOW PH TISSUE ENVIRONMENTS OR CELLULAR COMPARTMENTS AND METHODS OF USE THEREOF

CROSS REFERENCE TO RELATED APPLICATIONS

This application claims priority to U.S. Ser. No. 14/293,733 filed Jun. 2, 2014, by W. Mark Saltzman, Zhaozhong Jiang and Jiangbing Zhou, which claims priority to PCT/US2012/067447 filed Nov. 30, 2012, which claims priority to U.S. Provisional Application No. 61/566,412 entitled "Enzymatic Synthesis of Novel poly(amine-co-esters) and Their Use as Highly Efficient Non-viral Vectors for Gene Delivery" filed Dec. 2, 2011. U.S. Ser. No. 14/293,733 also claims priority to U.S. Provisional Application No. 61/870,497 filed Aug. 27, 2013.

STATEMENT REGARDING FEDERALLY SPONSORED RESEARCH OR DEVELOPMENT

This invention was made with government support under CA149128 and EB000487 awarded by National Institutes of Health. The government has certain rights in the invention.

FIELD OF THE INVENTION

The field of the invention is generally related to polymer compositions and methods for improved systemic delivery of diagnostic, prophylactic and/or therapeutic agents in vitro and in vivo, targeted to low pH tissue environments or cellular compartments.

BACKGROUND OF THE INVENTION

Non-viral vectors for gene delivery have attracted much attention in the past several decades due to their potential for limited immunogenicity, ability to accommodate and deliver large size genetic materials, and potential for modification of their surface structures. Major categories of non-viral vectors include cationic lipids and cationic polymers. Cationic lipid-derived vectors, which were pioneered by Feigner and colleagues, represent some of the most extensively investigated systems for non-viral gene delivery (Feigner, et al. Lipofection: a highly efficient, lipid-mediated DNA-transfection procedure. *PNAS*, 84, 7413-7417 (1987)) (Templeton, et al. Improved DNA:liposome complexes for increased systemic delivery and gene expression. *Nat. Biotechnol.* 15, 647-652 (1997)) (Chen, et al. Targeted nanoparticles deliver siRNA to melanoma. *J. Invest. Dermatol.* 130, 2790-2798 (2010)).

Cationic polymer non-viral vectors have gained increasing attention because of flexibility in their synthesis and structural modifications for specific biomedical applications. Both cationic lipid and cationic polymer systems deliver genes by forming condensed complexes with negatively charged DNA through electrostatic interactions: complex formation protects DNA from degradation and facilitates its cellular uptake and intracellular traffic into the nucleus.

Polyplexes formed between cationic polymers and DNA are generally more stable than lipoplexes formed between cationic lipids and DNA, but both are often unstable in physiological fluids, which contain serum components and salts, and tend to cause the complexes to break apart or aggregate (Al-Dosari, et al. *AAPS J.* 11, 671-681 (2009)) (Tros de Ilarduya, et al. *Eur. J. Pharm. Sci.* 40, 159-170 (2010)). Additionally, although some work indicates that anionic polymers or even naked DNA can provide some level of transfection under certain conditions, transfection by both lipids and polymers usually requires materials with excess charge, resulting in polyplexes or lipoplexes with net positive charges on the surface (Nicol, et al. *Gene. Ther.* 9, 1351-1358 (2002)) (Schlegel, et al. *J. Contr. Rel.* 152, 393-401 (2011)) (Liu, et al, *AAPS J.* 9, E92-E104 (2007)) (Liu, et al. *Gene Ther.* 6, 1258-1266 (1999)). When injected into the circulatory system in vivo, the positive surface charge initiates rapid formation of complex aggregates with negatively charged serum molecules or membranes of cellular components, which are then cleared by the reticuloendothelial system (RES).

More importantly, many cationic vectors developed so far exhibit substantial toxicity, which has limited their clinical applicability (Tros de Ilarduya, et al. *Eur. J. Pharm. Sci.* 40, 159-170 (2010)) (Gao, et al. *Biomaterials* 32, 8613-8625 (2011)) (Feigner, et al. *J. Biol. Chem.* 269, 2550-2561 (1994)) (Kafil, et al. *BioImpacts* 1, 23-30 (2011)) (Lv, et al. *J Contr. Rel.* 114, 100-109 (2006)). This too appears to depend on charge: excess positive charges on the surface of the complexes can interact with cellular components, such as cell membranes, and inhibit normal cellular processes, such as clathrin-mediated endocytosis, activity of ion channels, membrane receptors, and enzymes or cell survival signaling (Gao, et al. *Biomaterials* 32, 8613-8625 (2011)) (Feigner, et al. *J. Biol. Chem.* 269, 2550-2561 (1994)) (Kafil, et al. *BioImpacts* 1, 23-30 (2011)).

As a result, cationic lipids often cause acute inflammatory responses in animals and humans, whereas cationic polymers, such as PEI, destabilize the plasma-membrane of red blood cells and induce cell necrosis, apoptosis and autophagy (Tros de Ilarduya, et al. Gene delivery by lipoplexes and polyplexes. *Eur. J. Pharm. Sci.* 40, 159-170 (2010)) (Gao, et al. *Biomaterials* 32, 8613-8625 (2011)) (Lv, et al. *J. Contr. Rel.* 114, 100-109 (2006)). Because of these undesirable effects, there is a need for highly efficient non-viral vectors that have lower charge densities.

Synthesis of a family of biodegradable poly(amine-co-esters) formed via enzymatic copolymerization of diesters with amino-substituted diols is discussed in Liu, et al. *J. Biomed. Mater. Res.* A 96A, 456-465 (2011) and Jiang, Z. *Biomacromolecules* 11, 1089-1093 (2010).

Diesters with various chain length (e.g., from succinate to dodecanedioate) were copolymerized with diethanolamines with either an alkyl (methyl, ethyl, n-butyl, t-butyl) or an aryl (phenyl) substituent on the nitrogen. The high tolerance of the lipase catalyst allowed the copolymerization reactions to complete in one step without protection and deprotection of the amino functional groups. Upon protonation at slightly acidic conditions, these poly(amine-co-esters) readily condense DNA and form nano-sized polyplexes. Screening studies revealed that one of these materials, poly(N-methyldiethyleneamine sebacate) (PMSC), transfected a variety of cells including HEK293, U87-MG, and 9L, with efficiency comparable to that of leading commercial products, such as Lipofectamine 2000 and PEI14. PMSC had been previously used for gene delivery, but the delivery efficiency of the enzymatically synthesized materials was approximately five orders of magnitude higher than any previously reported (Wang, et al. *Biomacromolecules* 8, 1028-1037 (2007)) (Wang, et al. *Biomaterials* 28, 5358-5368 (2007)). However, these poly(amine-co-esters) were not effective for systemic delivery of nucleic acids in vivo. This may be due to the fact that the polyplexes formed by these polymers and genetic materials (1) do not have sufficient efficiency for in vivo applications and/or (2) are not stable enough in the blood and fall apart or aggregate during circulation.

Accordingly, there remains a need for non-viral vectors suitable for efficient systemic in vivo delivery of nucleic acids with low toxicity.

There is also a need for formulations of polymeric nanocarriers which can be prepared in as few steps as possible and in which the molecular weight and/or polymer composition can be easily controlled.

Therefore, it is an object of the invention to provide formulations that have improved polymers that can effectively deliver therapeutic, diagnostic, and/or prophylactic agents in vivo, and methods of making and using thereof.

It is an object of the invention to provide formulations that have improved polymers that can effectively deliver therapeutic, diagnostic, and/or prophylactic agents to tissues with low pH tissue environments or cellular compartments in high efficiency in vitro and are suitable for in vivo delivery of agents.

It is an object of the invention to provide methods of making formulations that have improved polymers for systemic delivery of therapeutic, diagnostic, and/or prophylactic agents to low pH tissue environments or cellular compartments in high efficiency in vitro and are suitable for in vivo delivery of agents.

It is also an object of the invention to provide methods of using formulations that improved polymers for systemic delivery of therapeutic, diagnostic, and/or prophylactic agents to low pH tissue environments or cellular compartments in high efficiency in vitro and are suitable for in vivo delivery of agents.

SUMMARY OF THE INVENTION

Formulations containing polymers with improved properties for delivering therapeutic, diagnostic, and/or prophylactic agents are described.

The polymers in the formulations, have the following formula:

Formula I

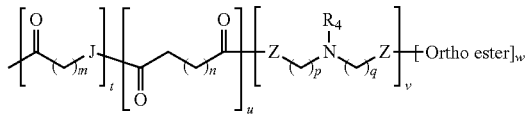

The ortho ester can have the structure shown below:

Formula II

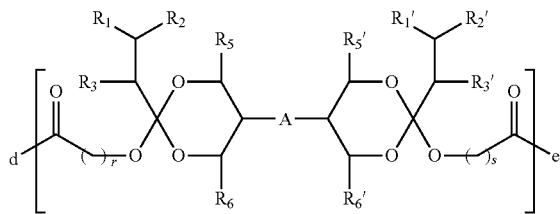

wherein the ortho ester is connected to the rest of the polymer at points d and e, each occurrence of m is an integer from 1-30,
each occurrence of n, p, q, r and s is independently an integer from 1-20, and
each occurrence of t, u, v, and w is independently an integer from 1-1000,
d, e, J and Z are independently O or NR', wherein R' is hydrogen, substituted or unsubstituted alkyl, or substituted or unsubstituted aryl. $R_1$, $R_1'$, $R_2$, $R_2'$, $R_3$, $R_3'$, $R_4$, $R_4'$, $R_5$, $R_5'$, $R_6$ and $R_6'$ are, independently, hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats. Representative $R_1$, $R_1'$, $R_2$, $R_2'$, $R_3$, $R_3'$, $R_4$, $R_4'$, $R_5$, $R_5'$, $R_6$ and $R_6'$ groups are alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, A is absent or A is a single bond.
In some embodiments, J and Z are each O.
In some embodiments, J and Z are each O, and m is an integer from 1-16, such as 4, 10, 13, or 14.
In some embodiments, J and Z are each O, m is an integer from 1-16, such as 4, 10, 13, or 14, and n is an integer from 1-10, such as 4, 5, 6, 7, or 8.
In some embodiments, J and Z are each O, m is an integer from 1-16, such as 4, 10, 13, or 14, n is an integer from 1-10, such as 4, 5, 6, 7, or 8, and p and q are the same integer from 1-6, such 2, 3, or 4.
In some embodiments, J and Z are each O, m is an integer from 1-16, such as 4, 10, 13, or 14, n is an integer from 1-10, such as 4, 5, 6, 7, or 8, and $R_4$ is alkyl, such a methyl, ethyl, n-propyl, isopropyl, n-butyl, or t-butyl, or aryl, such as phenyl.
In some embodiments, J and Z are each O, m is an integer from 1-16, such as 4, 10, 13, or 14, n is an integer from 1-10, such as 4, 5, 6, 7, or 8, $R_4$ is alkyl, such a methyl, ethyl, n-propyl, isopropyl, n-butyl, or t-butyl, or aryl, such as phenyl, and r and s are the same integer from 1-20, such as 1, 5 or 9.
In some embodiments, J and Z are each O, m is an integer from 1-16, such as 4, 10, 13, or 14, n is an integer from 1-10, such as 4, 5, 6, 7, or 8, $R_4$ is alkyl, such a methyl, ethyl, n-propyl, isopropyl, n-butyl, or t-butyl, or aryl, such as phenyl, r and s are the same integer from 1-20, such as 1, 5 or 9, and $R_1$, $R_1'$, $R_2$, $R_2'$, $R_3$, $R_3'$, $R_4$, $R_4'$, $R_5$, $R_5'$, $R_6$ and $R_6'$ are each a hydrogen atom.

In certain embodiments, m is 14 (e.g., pentadecalactone, PDL), n is 7 (e.g., diethylsebacate, DES), p and q are 2, and $R_4$ is methyl (e.g., N-methyldiethanolamine, MEDA), r and s are 1 (e.g. 2,2'-((3,9-diethyl-2,4,8,10-tetraoxaspiro[5.5]undecane-3,9-diyl)bis(oxy))diacetate), r and s are 5 (e.g. 6,6'-((3,9-diethyl-2,4,8,10-tetraoxaspiro[5.5]undecane-3,9-diyl)bis(oxy))dihexanoate), and r and s are 9 (9,9'-((3,9-diethyl-2,4,8,10-tetraoxaspiro[5.5]undecane-3,9-diyl)bis(oxy))dinonanoate).

In certain embodiments, the ortho ester unit has one ortho ester functional group including, but not limited to, the structures shown below:

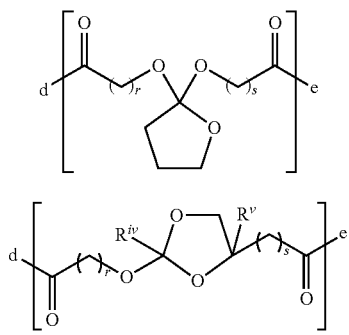

Formula III

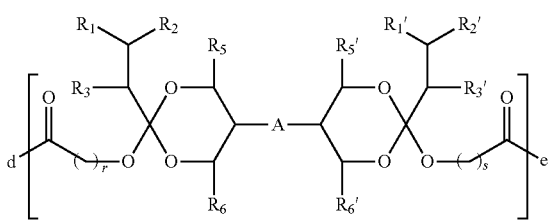

Formula II wherein the ortho ester is connected to the rest of the polymer at points d and e, as defined above. r and s are as defined above.

$R^{iv}$ and $R^{v}$ are independently a hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats. Representative $R^{iv}$ and $R^{v}$ groups are alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

The arrangements of the units within the polymer can be ordered or random.

In certain embodiments, m, n, p, q, r and s are as defined above, and PEG is incorporated as a monomer.

The polymer is preferably biocompatible. Readily available lactones of various ring sizes are known to possess low toxicity: for example, polyesters prepared from small lactones, such as poly(caprolactone) and poly(p-dioxanone) are commercially available biomaterials which have been used in clinical applications. Large (e.g., $C_{16}$-$C_{24}$) lactones and their polyester derivatives are natural products that have been identified in living organisms, such as bees.

The polymers can further include a block of an alkylene oxide, such as polyethylene oxide, polypropylene oxide, and/or polyethylene oxide-co-polypropylene oxide. The structure of a PEG-containing diblock polymer is shown below:

The ortho ester can have the structure shown below:

wherein the ortho ester is connected to the rest of the polymer at points d and e. A is a single bond, or A is absent, m is an integer from 1-30, n, p, and q are independently an integer from 1-20, t, u, v, w and x are independently integers from 1-1000, and J and Z are independently O or NR', wherein R' is hydrogen, substituted or unsubstituted alkyl, or substituted or unsubstituted aryl. In particular embodiments, the values of t, u, v, w and x are such that the weight average molecular weight of the polymer is greater than 1,000 Daltons, preferably greater than 5,000 Daltons.

In certain embodiments, the ortho ester unit has one ortho ester functional group including, but not limited to, the structures shown below:

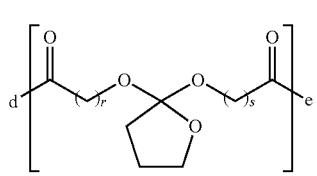

Formula III

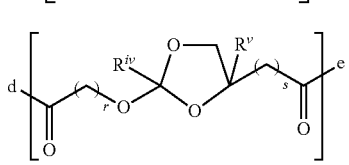

Formula IV wherein the ortho ester is connected to the rest of the polymer at points d and e as defined above. r and s are as defined above.

$R^{iv}$ and $R^{v}$ are independently a hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats. Representative $R^{iv}$ and $R^{v}$ groups are alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substi-

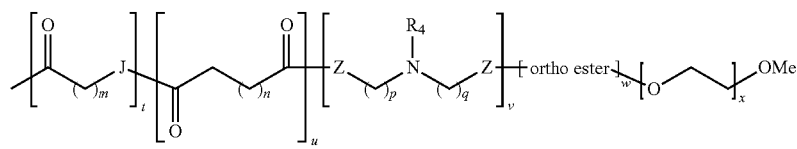

tuted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

The arrangements of the units within the polymer can be ordered or random.

The structure of a PEG-containing triblock copolymer is shown below:

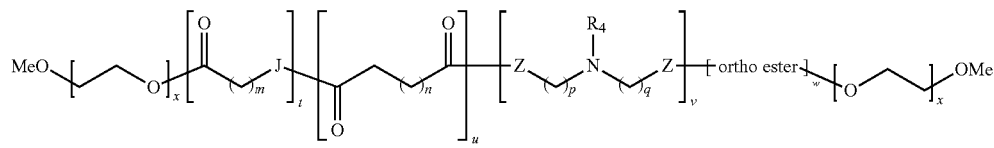

The ortho ester can have the structure shown below:

Formula II

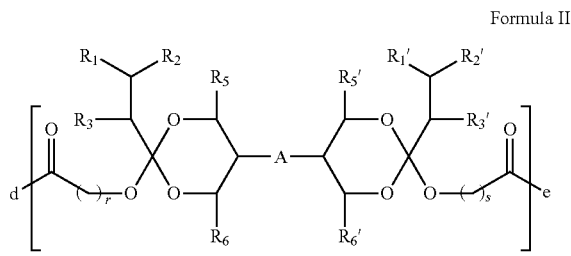

wherein the ortho ester is connected to the rest of the polymer at points d and e as defined above. A is a single bond, or A is absent, m is an integer from 1-30, n, p and q are independently an integer from 1-20, t, u, v, w and x are independently integers from 1-1000, and J and Z are independently O or NW, wherein R' is hydrogen, substituted or unsubstituted alkyl, or substituted or unsubstituted aryl. In particular embodiments, the values of t, u, v, w and x are such that the weight average molecular weight of the polymer is greater than 1,000 Daltons, preferably greater than 5,000 Daltons.

In certain embodiments, the ortho ester unit has one ortho ester functional group including, but not limited to, the structures shown below:

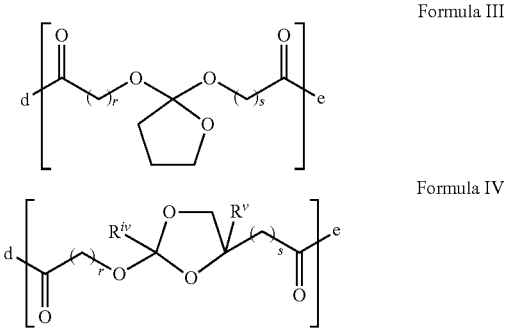

wherein the ortho ester is connected to the rest of the polymer at points d and e as defined above. r and s are as defined above.

$R^{iv}$ and $R^v$ are independently a hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats. Representative $R^{iv}$ and $R^v$ groups are alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

The arrangements of the units within the polymer can be ordered or random.

The blocks of polyalkylene oxide can located at the termini of the polymer (i.e., by reacting PEG having one hydroxy group blocked, for example, with a methoxy group), within the polymer backbone (i.e., neither of the hydroxyl groups are blocked), or combinations thereof.

In particular embodiments, the values of t, u, v, w and/or x are such that the weight average molecular weight of the polymer is greater than 1,000 Daltons, preferably greater than 5,000 Daltons.

The polymer can prepared from one or more lactones, one or more amine-diols (Z=O) or triamines (Z=NR'), one or more diacids or diesters, and one or more orthoesters. In those embodiments where two or more different lactone, diacid or diester, triamine or amine-diol and/or orthoester monomers are used, then the values of m, n, p, q, r and/or s can be the same or different.

The monomers shown above can be unsubstituted or can be substituted. "Substituted", as used herein, means one or more atoms or groups of atoms on the monomer has been replaced with one or more atoms or groups of atoms which are different than the atom or group of atoms being replaced. In some embodiments, the one or more hydrogens on the monomer is replaced with one or more atoms or groups of atoms. Examples of functional groups which can replace hydrogen are listed above in the definition. In some embodiments, one or more functional groups can be added which vary the chemical and/or physical property of the resulting monomer/polymer, such as charge or hydrophilicity/hydrophobicity, etc. Exemplary substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amino, amidine, imine, cyano, nitro, azido, sulfhydryl, alkylthio, sulfate, sulfonate, sulfamoyl, sulfonamido, sulfonyl, nitro, heterocyclyl, aralkyl, or an aromatic or heteroaromatic moiety.

The polymers can be used to form micro- and/or nanoparticles having encapsulated therein therapeutic, diagnostic, and/or prophylactic agent. The agent to be encapsulated and delivered can be a small molecule agent (i.e., nonpolymeric agent having a molecular weight less than 2,000, 1500, 1,000, 750, or 500 Dalton) or a macromolecule (e.g., an oligomer or polymer) such as proteins, enzymes, peptides, nucleic acids, etc. The particles can be used for in vivo and/or in vitro delivery of the agent.

The particles prepared from the polymers can be coated with surface charge altering materials, such as polypeptides, that increase stability and half-life of the particles in systemic circulation. The charge altering material can include a targeting moiety that increases targeting of the particles to a cell type or cell state of interest.

In some embodiments, the particles have a mean particle size from about 100 nm to about 300 nm, preferably from about 150 nm to about 275 nm. In some embodiments, the weight:weight ratio of polymer:polynucleotide is between about 25:1 and 250:1.

In some embodiments, the polymers can be used to form polymeric nanoparticulate polynucleotide carriers, referred to herein as polyplexes, which are effective for delivering the polynucleotides to cells in vitro and in vivo. The polyplexes have improved efficacy or reduced toxicity in vivo compared to other polynucleotide delivery approaches, enabling the polyplexes to be utilized in a broad range of therapeutic applications, for example, gene therapy. Typically, the polyplexes are less toxic and more efficient at transfecting polynucleotides when compared to a control, such as LIPOFECTAMINE 2000 or polyethylenimine (PEI). In some embodiments, the polyplexes are suitable for in vivo transfection, and can be used when other transfection reagents are too toxic or too inefficient to support in vivo applications. In some embodiments, the in vivo application includes systemic administration of the polyplexes.

The polyplexes can be coated with one or more agents that reduce the surface charge of the polyplex at physiological pH. The coating can impart a neutral or negative surface charge to the polyplex. The agent can include, for example, a polypeptide with a series of negatively charged amino acids, such as glutamic acids or aspartic acids. In some embodiments, the polypeptide includes a cell targeting signal or cell targeting domain that enhances targeting of the polyplexes to a specific cell-type or cell-state. For example, the cell targeting domain can enhance targeting of the polyplexes to cancer cells. Exemplary cell targeting domains include RGD, R/KxxR/K where "x" is any amino acid, GdPdLGdVdRG (SEQ ID NO:5), and ASGPR (SEQ ID NO:6). In some embodiments, the stretch of negatively charged amino acids and the cell targeting domain are linked by a linker polypeptide. The linker can be a series of glycines. An exemplary coating including an agent that reduces surface charge and provides cell specific targeting to cancer cells is EEEEEEEEEEEEEEEEGGGGGGRGDK (SEQ ID NO:1).

The polynucleotide can include a sequence that encodes a protein, a sequence that encodes a functional nucleic acid, or can itself be a functional nucleic acid, rRNA, or tRNA. Functional nucleic acids include, but are not limited to, antisense molecules, siRNA, miRNA, aptamers, ribozymes, triplex forming molecules, RNAi, and external guide sequences. In some embodiments, the polynucleotide includes an expression control sequence operably linked to a sequence encoding a protein, functional nucleic acid, rRNA, or tRNA. For example, the polynucleotide can be an expression vector.

Compositions, such as pharmaceutical compositions, containing the particles are also disclosed. The particles can be contacted with cells to transfect the agent, such as a polynucleotide, into the cells. In some embodiments, the contacting occurs in vivo by administering the particles, or a pharmaceutical composition containing the particles, to a subject in an effective amount to treat a disease or condition. The disease or condition can be, for example, a mitochondrial disease, an infectious disease, a cancer, a metabolic disorder, an autoimmune disease, an inflammatory disorder, or an age-related disorder. The particles can be administered parenterally, topically, or transmucosally (eye, lung, nasal, vaginal, rectal). The particles can be administered systemically or locally.

In some embodiments, contacting the cells with polyplexes to transfect the polynucleotide occurs in vitro, or ex vivo. The cells can be primary cells or cells from a cell line. The primary cells can be harvested from a subject. In some embodiments, the transfected cells are administered back to the subject, or to a different subject as part of a cell-based therapy for treating a disease or condition.

DETAILED DESCRIPTION OF THE INVENTION

I. Definitions

Figure 1:
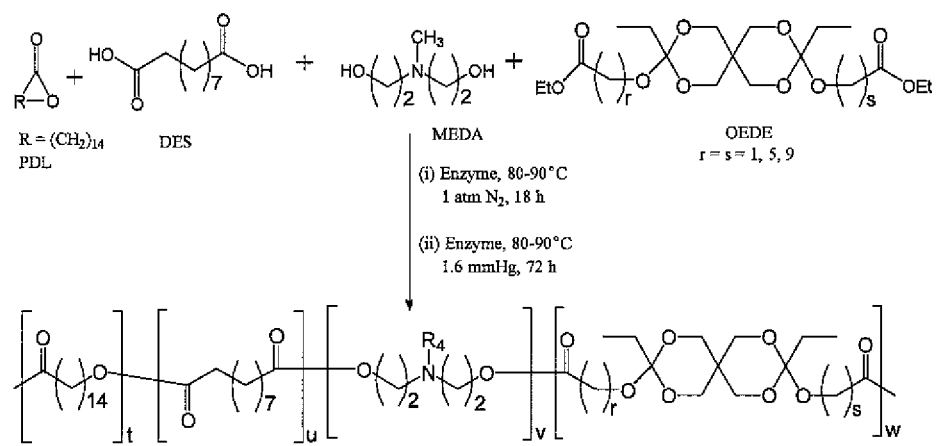
FIG. 1 is a scheme showing a two-stage process for the preparation of quaterpolymers from a PDL, DES, MEDE and three ortho esters.

The term "polyplex" as used herein refers to polymeric micro- and/or nanoparticles or micelles having encapsulated therein, dispersed within, and/or associated with the surface of, one or more polynucleotides.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

The terms "subject," "individual," and "patient" refer to any individual who is the target of treatment using the disclosed compositions. The subject can be a vertebrate, for example, a mammal. Thus, the subject can be a human. The subjects can be symptomatic or asymptomatic. The term does not denote a particular age or sex. Thus, adult and newborn subjects, whether male or female, are intended to be covered. A subject can include a control subject or a test subject.

The term "biocompatible" as used herein refers to one or more materials that are neither themselves toxic to the host (e.g., an animal or human), nor degrade (if the material degrades) at a rate that produces monomeric or oligomeric subunits or other byproducts at toxic concentrations in the host.

The term "biodegradable" as used herein means that the materials degrades or breaks down into its component subunits, or digestion, e.g., by a biochemical process, of the material into smaller (e.g., non-polymeric) subunits.

The term "diameter" is art-recognized and is used herein to refer to either of the physical diameter or the hydrodynamic diameter. The diameter of an essentially spherical particle may refer to the physical or hydrodynamic diameter. The diameter of a nonspherical particle may refer preferentially to the hydrodynamic diameter. As used herein, the diameter of a non-spherical particle may refer to the largest linear distance between two points on the surface of the particle. When referring to multiple particles, the diameter of the particles typically refers to the average diameter of the particles. Particle diameter can be measured using a variety of techniques in the art including, but not limited to, dynamic light scattering.

"Sustained release" as used herein refers to release of a substance over an extended period of time in contrast to a bolus type administration in which the entire amount of the substance is made biologically available at one time.

The term "microspheres" is art-recognized, and includes substantially spherical colloidal structures, e.g., formed from biocompatible polymers such as subject compositions, having a size ranging from about one or greater up to about 1000 microns. In general, "microcapsules," also an art-recognized term, may be distinguished from microspheres, because microcapsules are generally covered by a substance of some type, such as a polymeric formulation. The term "microparticles" is also art-recognized, and includes microspheres and microcapsules, as well as structures that may not be readily placed into either of the above two categories, all with dimensions on average of less than about 1000 microns. A microparticle may be spherical or nonspherical and may have any regular or irregular shape. If the structures are less than about one micron (1000 nm) in diameter, then the corresponding art-recognized terms "nanosphere," "nanocapsule," and "nanoparticle" may be utilized. In certain embodiments, the nanospheres, nanocapsules and nanoparticles have an average diameter of about 500 nm, 200 nm, 100 nm, 50 nm, 10 nm, or 1 nm. In some embodiments, the average diameter of the particles is from about 200 nm to about 600 nm, preferably from about 200 to about 500 nm. Microparticles can be used for gene therapy, particularly for vaccinations.

A composition containing microparticles or nanoparticles may include particles of a range of particle sizes. In certain embodiments, the particle size distribution may be uniform, e.g., within less than about a 20% standard deviation of the mean volume diameter, and in other embodiments, still more uniform, e.g., within about 10%, 8%, 5%, 3%, or 2% of the median volume diameter.

The term "particle" as used herein refers to any particle formed of, having attached thereon or thereto, or incorporating a therapeutic, diagnostic or prophylactic agent, optionally including one or more polymers, liposomes micelles, or other structural material. A particle may be spherical or nonspherical. A particle may be used, for example, for diagnosing a disease or condition, treating a disease or condition, or preventing a disease or condition.

The phrases "parenteral administration" and "administered parenterally" are art-recognized terms, and include modes of administration other than enteral and topical administration, such as injections, and include without limitation intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "surfactant" as used herein refers to an agent that lowers the surface tension of a liquid.

The term "targeting moiety" as used herein refers to a moiety that localizes to or away from a specific locale. The moiety may be, for example, a protein, nucleic acid, nucleic acid analog, carbohydrate, or small molecule. Said entity may be, for example, a therapeutic compound such as a small molecule, or a diagnostic entity such as a detectable label. Said locale may be a tissue, a particular cell type, or a subcellular compartment. In one embodiment, the targeting moiety directs the localization of an active entity. The active entity may be a small molecule, protein, polymer, or metal. The active entity may be useful for therapeutic, prophylactic, or diagnostic purposes.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. Likewise, preferred cycloalkyls have from 3-10 carbon atoms in their ring structure, and more preferably have 5, 6, or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Cycloalkyls can be substituted in the same manner.

"Aryl", as used herein, refers to C$_5$-C$_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1, 5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, a "promoter site" is a sequence of nucleotides to which an RNA polymerase, such as the DNA-dependent RNA polymerase originally isolated from bacteriophage, described by Davanloo, et al., *Proc. Natl. Acad. Sci. USA,* 81:2035-39 (1984), or from another source, binds with high specificity, as described by Chamberlin, et al., *Nature,* 228:227-231 (1970).

As used herein, a "poly(A)" is a series of adenosines attached by polyadenylation to the mRNA. In the preferred embodiment of a construct for transient expression, the polyA is between 50 and 5000, preferably greater than 64, more preferably greater than 100, most preferably greater than 300 or 400. poly(A) sequences can be modified chemically or enzymatically to modulate mRNA functionality such as localization, stability or efficiency of translation.

As used herein, an "open reading frame" or "ORF" is a series of nucleotides that contains a sequence of bases that could potentially encode a polypeptide or protein. An open reading frame is located between the start-code sequence (initiation codon or start codon) and the stop-codon sequence (termination codon).

The term "construct" refers to a recombinant genetic molecule having one or more isolated polynucleotide sequences.

The term "expression control sequence" refers to a nucleic acid sequence that controls and regulates the transcription and/or translation of another nucleic acid sequence. Control sequences that are suitable for prokaryotes, for example, include a promoter, optionally an operator sequence, a ribosome binding site, and the like. Eukaryotic cells are known to utilize promoters, polyadenylation signals, and enhancers.

As used herein "to reprogram a cell" or "cellular reprogramming" means to induce a cell to express one or more polypeptides or functional nucleic acids in an effective amount to change a function of the cell. The function can be any function. For example, an immune cell can be induced to express a receptor which changes the cell's ability to recognize an antigen or to mediate an immune response; or a somatic cell can be induced to express a pluripopency marker(s) which can dedifferentiate the cell from a somatic state to a pluripotent state (i.e., induced pluripotent stem cell (iPS)).

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will assist the linked protein to be localized at the specific organelle.

A "transgenic organism" as used herein, is any organism, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. Suitable transgenic organisms include, but are not limited to, bacteria, cyanobacteria, fungi, plants and animals. The nucleic acids described herein can be introduced into the host by methods known in the art, for example infection, transfection, transformation or transconjugation. Techniques for transferring DNA into such organisms are widely known and provided in references such as Sambrook, et al. (2000) Molecular Cloning: A Laboratory Manual, 3$^{rd}$ ed., vol. 1-3, Cold Spring Harbor Press, Plainview N.Y.

As used herein, the term "eukaryote" or "eukaryotic" refers to organisms or cells or tissues derived therefrom belonging to the phylogenetic domain Eukarya such as animals (e.g., mammals, insects, reptiles, and birds), ciliates, plants (e.g., monocots, dicots, and algae), fungi, yeasts, flagellates, microsporidia, and protists.

As used herein, the term "non-eukaryotic organism" refers to organisms including, but not limited to, organisms of the Eubacteria phylogenetic domain, such as *Escherichia coli, Thermus thermophilus*, and *Bacillus stearothermophilus*, or organisms of the Archaea phylogenetic domain such as, *Methanocaldococcus jannaschii, Methanothermobacter thermautotrophicus, Halobacterium* such as *Haloferax vokanii* and *Halobacterium* species NRC-1, *Archaeoglobus fulgidus, Pyrococcus furiosus, Pyrococcus horikoshii*, and *Aeuropyrum Pernix*.

The term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

The term "orthologous genes" or "orthologs" refer to genes that have a similar nucleic acid sequence because they were separated by a speciation event.

The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides which do not significantly alter the characteristics of the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "isolated" is meant to describe a compound of interest (e.g., nucleic acids) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids are at least 60% free, preferably 75% free, and most preferably 90% free from other associated components.

The term "vector" refers to a replicon, such as a plasmid, phage, or cosmid, into which another DNA segment may be inserted so as to bring about the replication of the inserted segment. The vectors can be expression vectors.

The term "expression vector" refers to a vector that includes one or more expression control sequences.

"Transformed," "transgenic," "transfected" and "recombinant" refer to a host organism into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a cell, bacterium or plant, which does not contain the heterologous nucleic acid molecule.

The term "endogenous" with regard to a nucleic acid refers to nucleic acids normally present in the host.

The term "heterologous" refers to elements occurring where they are not normally found. For example, a promoter may be linked to a heterologous nucleic acid sequence, e.g., a sequence that is not normally found operably linked to the promoter. When used herein to describe a promoter element, heterologous means a promoter element that differs from that normally found in the native promoter, either in sequence, species, or number. For example, a heterologous control element in a promoter sequence may be a control/regulatory element of a different promoter added to enhance promoter control, or an additional control element of the same promoter. The term "heterologous" thus can also encompass "exogenous" and "non-native" elements.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "purified" and like terms relate to the isolation of a molecule or compound in a form that is substantially free (at least 60% free, preferably 75% free, and most preferably 90% free) from other components normally associated with the molecule or compound in a native environment.

Unless otherwise indicated, the disclosure encompasses conventional techniques of molecular biology, microbiology, cell biology and recombinant DNA, which are within the skill of the art. See, e.g., Sambrook and Russell, Molecular Cloning: A Laboratory Manual, 3rd edition (2001); Current Protocols In Molecular Biology [(Ausubel, et al. eds., (1987)]; Coligan, Dunn, Ploegh, Speicher and Wingfeld, eds. (1995) Current Protocols in Protein Science (John Wiley & Sons, Inc.); the series Methods in Enzymology (Academic Press, Inc.): PCR 2: A Practical Approach (M. J. MacPherson, B. D. Hames and G. R. Taylor eds. (1995)].

II. Formulations

It has been discovered that the gene delivery ability of polycationic polymers is due to multiple factors, including polymer molecular weight, hydrophobicity, and charge density. Many synthetic polycationic materials have been tested as vectors for non-viral gene delivery, but almost all are ineffective due to their low efficiency or high toxicity. Most polycationic vectors described previously exhibit high charge density, which has been considered a major requirement for effective DNA condensation. As a result, they are able to deliver genes with high efficiency in vitro but are limited for in vivo applications because of toxicity related to the excessive charge density.

High molecular weight polymers, particularly quaterpolymers, and methods of making them using enzyme-catalyzed copolymerization of a lactone with a dialkyl diester, an amino diol and an ortho ester are disclosed. These poly (amine-co-ester-co-ortho ester) quaterpolymers have a low charge density. In addition, their hydrophobicity can be varied by selecting a lactone comonomer with specific ring size and by adjusting lactone content in the polymers. High molecular weight and increased hydrophobicity of the lactone-diester-amino diol-ortho ester quaterpolymers compensate for the low charge density to provide efficient gene delivery with minimal toxicity.

In preferred embodiments, the quaterpolymers exhibit efficient gene delivery with reduced toxicity. The quaterpolymers can be significantly more efficient the commercially available non-viral vectors. For examples, the quaterpolymers described herein can be more than 100× more efficient than commercially available non-viral vectors such as PEI and LIPOFECTAMINE 2000 based on luciferase expression assay while exhibiting minimal toxicity at doses of up to 0.5 mg/ml toxicity compared to these commercially available non-viral vectors. Preferably, the quaterpolymer is non-toxic at concentrations suitable for both in vitro and in vivo transfection of nucleic acids. For example, in some embodiments, the disclosed quaterpolymers cause less nonspecific cell death compared to other approaches of cell transfection.

A. Polymers

Poly(amine-co-ester-co-ortho esters) or poly(amine-co-amides-co-orthoesters) are described herein. The polymers in the formulations, have the following formula:

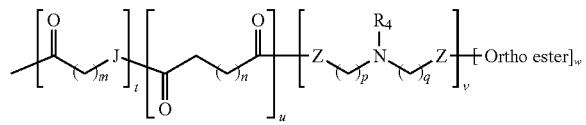

Formula I

The ortho ester can have the structure shown below:

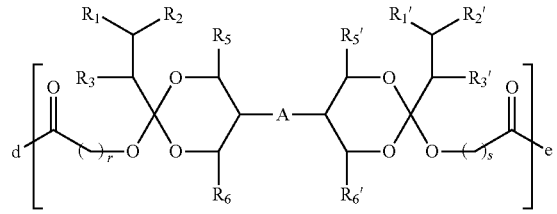

Formula II wherein the ortho ester is connected to the rest of the polymer at points d and e as defined above, each occurrence of m is an integer from 1-30, each occurrence of n, p, q, r and s is independently an integer from 1-20, and each occurrence of t, u, v, and w is independently an integer from 1-1000, J and Z are independently O or NR', wherein R' is hydrogen, substituted or unsubstituted alkyl, or substituted or unsubstituted aryl. $R_1$, $R_1'$, $R_2$, $R_2'$, $R_3$, $R_3'$, $R_4$, $R_4'$, $R_5$, $R_5'$, $R_6$ and $R_6'$ are, independently, hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats. Representative $R_1$, $R_1'$, $R_2$, $R_2'$, $R_3$, $R_3'$, $R_4$, $R_4'$, $R_5$, $R_5'$, $R_6$ and $R_6'$ groups are alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, A is absent or A is a single bond.

In some embodiments, J and Z are each O.

In some embodiments, J and Z are each O, and m is an integer from 1-16, such as 4, 10, 13, or 14.

In some embodiments, J and Z are each O, m is an integer from 1-16, such as 4, 10, 13, or 14, and n is an integer from 1-10, such as 4, 5, 6, 7, or 8.

In some embodiments, J and Z are each O, m is an integer from 1-16, such as 4, 10, 13, or 14, n is an integer from 1-10, such as 4, 5, 6, 7, or 8, and p and q are the same integer from 1-6, such 2, 3, or 4.

In some embodiments, J and Z are each O, m is an integer from 1-16, such as 4, 10, 13, or 14, n is an integer from 1-10, such as 4, 5, 6, 7, or 8, and $R_4$ is alkyl, such a methyl, ethyl, n-propyl, isopropyl, n-butyl, or t-butyl, or aryl, such as phenyl.

In some embodiments, J and Z are each O, m is an integer from 1-16, such as 4, 10, 13, or 14, n is an integer from 1-10, such as 4, 5, 6, 7, or 8, $R_4$ is alkyl, such a methyl, ethyl, n-propyl, isopropyl, n-butyl, or t-butyl, or aryl, such as phenyl, and r and s are the same integer from 1-20, such as 1, 5 or 9.

In some embodiments, J and Z are each O, m is an integer from 1-16, such as 4, 10, 13, or 14, n is an integer from 1-10, such as 4, 5, 6, 7, or 8, $R_4$ is alkyl, such a methyl, ethyl, n-propyl, isopropyl, n-butyl, or t-butyl, or aryl, such as phenyl, r and s are the same integer from 1-20, such as 1, 5 or 9, and $R_1$, $R_1'$, $R_2$, $R_2'$, $R_3$, $R_3'$, $R_4$, $R_4'$, $R_5$, $R_5'$, $R_6$ and $R_6'$ are each a hydrogen atom.

In certain embodiments, m is 14 (e.g., pentadecalactone, PDL), n is 7 (e.g., diethylsebacate, DES), p and q are 2, and $R_4$ is methyl (e.g., N-methyldiethanolamine, MEDA), r and s are 1 (e.g. 2,2'-((3,9-diethyl-2,4,8,10-tetraoxaspiro[5.5] undecane-3,9-diyl)bis(oxy))diacetate), r and s are 5 (e.g. 6,6'-((3,9-diethyl-2,4,8,10-tetraoxaspiro[5.5]undecane-3,9-diyl)bis(oxy))dihexanoate), and r and s are 9 (9,9'-((3,9-diethyl-2,4,8,10-tetraoxaspiro[5.5]undecane-3,9-diyl)bis (oxy))dinonanoate).

In certain embodiments, the ortho ester unit has one ortho ester functional group including, but not limited to, the structures shown below:

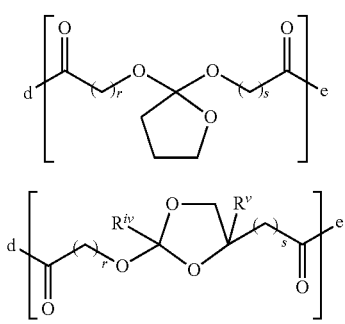

Formula III

Formula IV

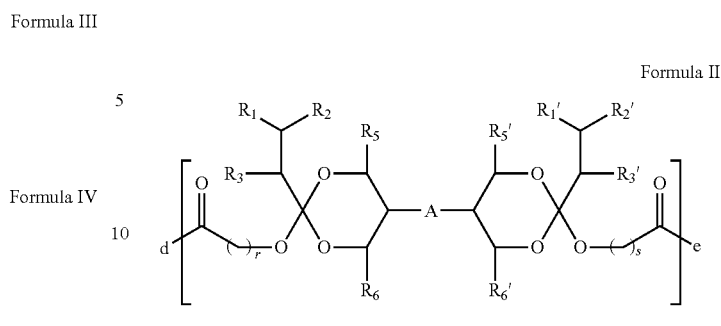

Formula II

The ortho ester can have the structure shown below:

wherein the ortho ester is connected to the rest of the polymer at points d and e as defined above. r and s are as defined above.

$R^{iv}$ and $R^v$ are independently a hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats. Representative $R^{iv}$ and $R^v$ groups are alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

The arrangements of the units within the polymer can be ordered or random.

In certain embodiments, m, n, p, q, r and s are as defined above, and PEG is incorporated as a monomer.

The polymer is preferably biocompatible. Readily available lactones of various ring sizes are known to possess low toxicity: for example, polyesters prepared from small lactones, such as poly(caprolactone) and polyp-dioxanone) are commercially available biomaterials which have been used in clinical applications. Large (e.g., $C_{16}$-$C_{24}$) lactones and their polyester derivatives are natural products that have been identified in living organisms, such as bees.

The polymers can further include a block of an alkylene oxide, such as polyethylene oxide, polypropylene oxide, and/or polyethylene oxide-co-polypropylene oxide. The structure of a PEG-containing diblock polymer is shown below:

wherein the ortho ester is connected to the rest of the polymer at points d and e as defined above. A is a single bond, or A is absent, m is an integer from 1-30, n, p, and q are independently an integer from 1-20, t, u, v, w and x are independently integers from 1-1000, and J and Z are independently O or NR', wherein R' is hydrogen, substituted or unsubstituted alkyl, or substituted or unsubstituted aryl. In particular embodiments, the values of t, u, v, w and x are such that the weight average molecular weight of the polymer is greater than 1,000 Daltons, preferably greater than 5,000 Daltons.

In certain embodiments, the ortho ester unit has one ortho ester functional group including, but not limited to, the structures shown below:

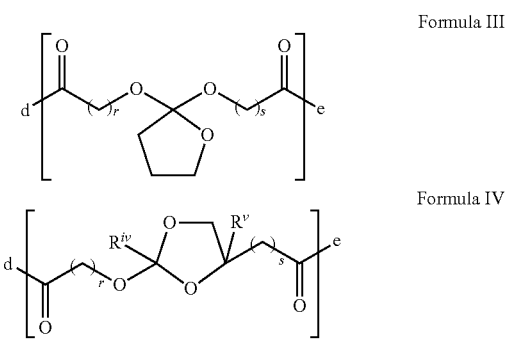

Formula III

Formula IV wherein the ortho ester is connected to the rest of the polymer at points d and e as defined above. r and s are as defined above.

$R^{iv}$ and $R^v$ are independently a hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural

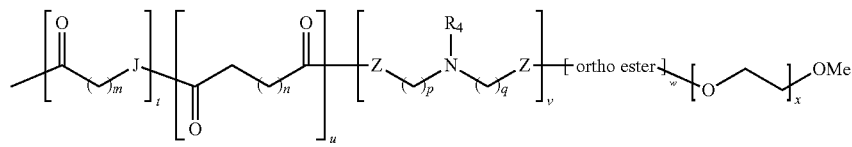

formats. Representative $R^{iv}$ and $R^v$ groups are alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

The arrangements of the units within the polymer can be ordered or random.

The structure of a PEG-containing triblock copolymer is shown below:

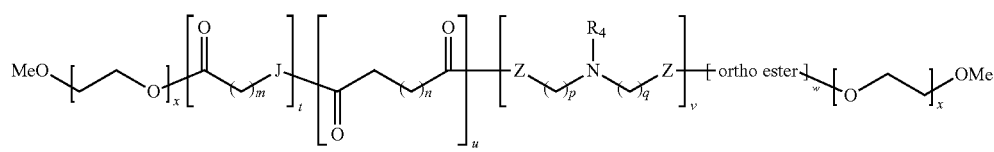

The ortho ester can have the structure shown below:

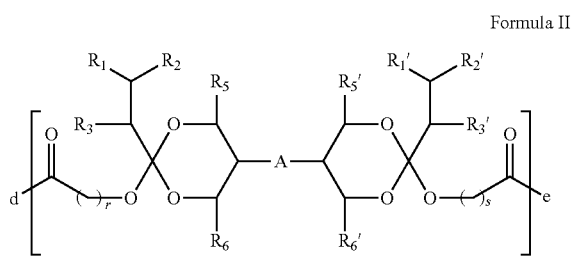

Formula II wherein the ortho ester is connected to the rest of the polymer at points d and e as defined above. A is a single bond, or A is absent, m is an integer from 1-30, n, p and q are independently an integer from 1-20, t, u, v, w and x are independently integers from 1-1000, and J and Z are independently O or NR', wherein R' is hydrogen, substituted or unsubstituted alkyl, or substituted or unsubstituted aryl. In particular embodiments, the values of t, u, v, w and x are such that the weight average molecular weight of the polymer is greater than 1,000 Daltons, preferably greater than 5,000 Daltons.

In certain embodiments, the ortho ester unit has one ortho ester functional group including, but not limited to, the structures shown below:

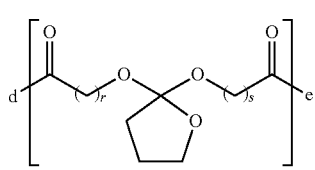

Formula III

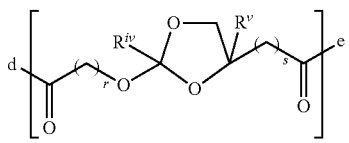

Formula IV wherein the ortho ester is connected to the rest of the polymer at points d and e as defined above. r and s are as defined above.

$R^{iv}$ and $R^v$ are independently a hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats. Representative $R^{iv}$ and $R^v$ groups are alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

The arrangements of the units within the polymer can be ordered or random.

The blocks of polyalkylene oxide can located at the termini of the polymer (i.e., by reacting PEG having one hydroxy group blocked, for example, with a methoxy group), within the polymer backbone (i.e., neither of the hydroxyl groups are blocked), or combinations thereof. The arrangements of the units within the polymer can be ordered or random.

Methods of Making the Polymers

Methods for the synthesis of the polymers from a lactone, a dialkyl ester, a dialkyl amine and an ortho ester using an enzyme catalyst, such as a lipase, are also provided. Exemplary lactones are shown in FIG. 1. In one embodiment, the polymers are prepared as shown in Scheme 1:

Scheme 1: Preparation of poly(amine-co-ester-co-ortho ester) quaterpolymers

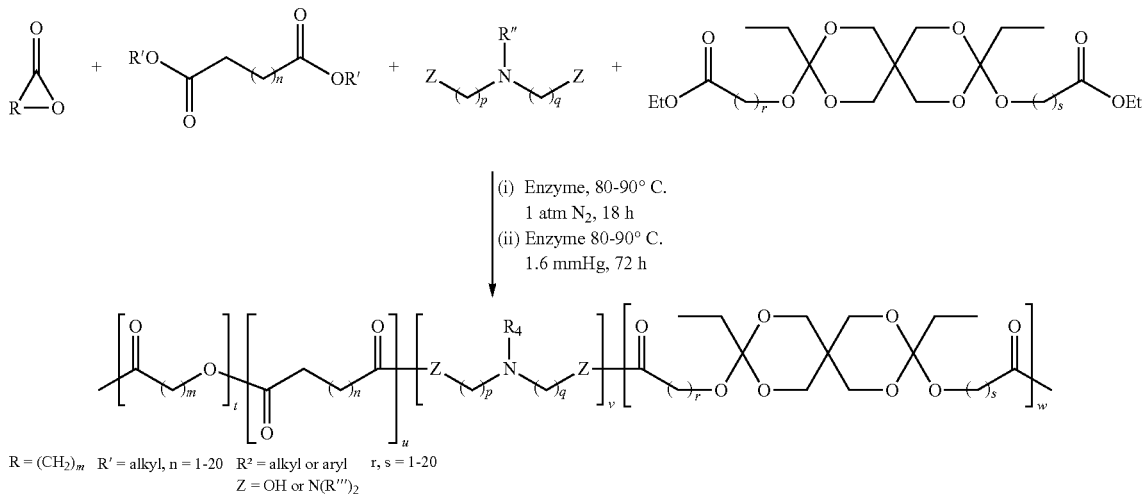

wherein m is an integer from 1-30, n, p, q, r and s are independently an integer from 1-20, and t, u, v, and w are independently integers from 1-1000. The polymer can prepared from one or more lactones, one or more amine-diols or triamines, one or more diacids or diesters, and one or more ortho esters. In those embodiments where two or more different lactone, diacid or diester, triamine or amine-diol and/or ortho ester monomers are used, then the values of m, n, p, q, r and/or s can be the same or different.

The synthesis of the polymers described herein using a lactone, diacid or diester, an amine diol or a triamine, an ortho ester, and PEG as reactants is shown in Scheme 2.

deprotection of the amino group(s). Such amino-bearing copolyesters are extremely difficult to prepare using conventional organometallic catalysts, as such catalysts are often sensitive to or deactivated by organic amines. These catalysts are also known to be inefficient for polymerizing large lactone ring monomers. Enzymatic catalysts have distinct advantages for producing biomedical polymers owing to the high activity and selectivity of the enzyme and the resulting high purity of products that are metal-free.

Exemplary polymers prepared from a lactone (co-pentadecalactone (PDL)), diethyl sebacate (DES), a dialkyl amine (e.g., N-methyldiethanolamine (MEDA)) and three ortho Scheme 2: Enzymatic Synthesis of Block Copolymers

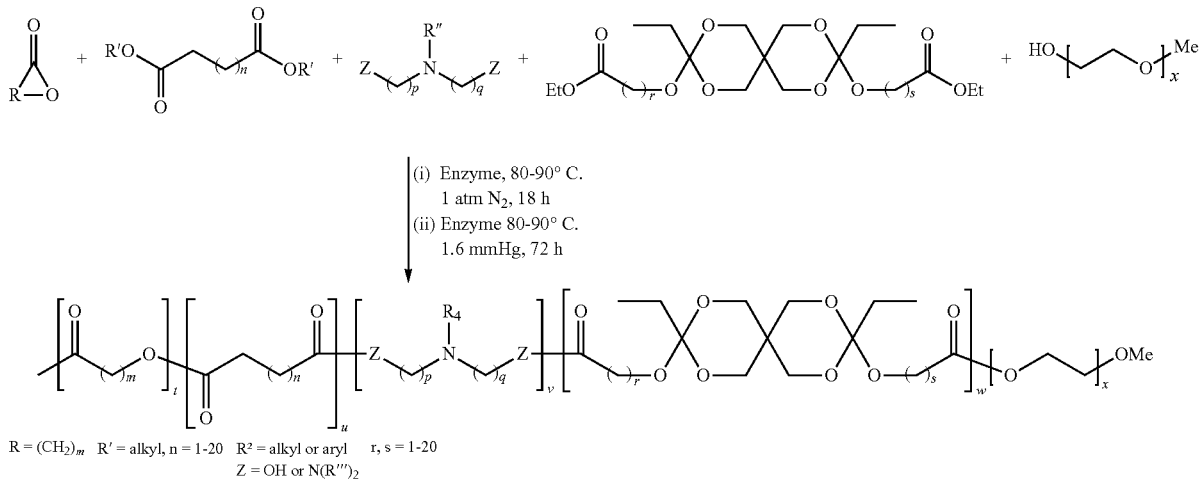

The enzymatic method described herein allows for the synthesis of polymers with diverse chain structures and tunable hydrophobicities. In some embodiments, the hydrophobicity is varied by varying the ring size and/or molar amount of the lactone monomer. Lactone with a wide range of ring sizes (e.g., $C_4$-$C_{24}$, preferably $C_6$-$C_{24}$, more preferably from $C_6$-$C_{16}$) can be used as comonomers. The reaction can be performed in a single step without protection and esters (2,2'-((3,9-diethyl-2,4,8,10-tetraoxaspiro[5.5]undecane-3,9-diyl)bis(oxy))diacetate, 6,6'-((3,9-diethyl-2,4,8,10-tetraoxaspiro[5.5]undecane-3,9-diyl)bis(oxy))dihexanoate, and 9,9'-((3,9-diethyl-2,4,8,10-tetraoxaspiro[5.5]undecane-3,9-diyl)bis(oxy))dinonanoate are described in Table 1 below. To simplify nomenclature, PACEO(a)-b is used to distinguish polymers with the different structures and contents of ortho esters. PACEO stands for poly(amineco-ester-co-ortho ester); "a" denotes the number of methylene groups between the ortho ester and the ester functional groups, and "b" denotes the percent content of the ortho ester present in the polymer.

TABLE 1

The composition, weight and number average molecular weights, and polydispersity of selected polymers

| Name | OEDE/DES/MEDA/PDL (feed molar ratio) | OEDE/DES/MEDA/PDL (unit molar ratio)* | Mw | Mn | Mw/Mn |
|---|---|---|---|---|---|
| PACEO(1)-10* | 10/90/100/10 | NA | 1777 | 1477 | 1.20 |
| PACEO(1)-20* | 20/80/100/10 | NA | 1827 | 1520 | 1.21 |
| PACEO(1)-30* | 30/70/100/10 | NA | 1874 | 1541 | 1.21 |
| PACEO(1)-40* | 40/60/100/10 | NA | 2169 | 1704 | 1.28 |
| PACEO(1)-50* | 50/50/100/10 | NA | 2064 | 1642 | 1.26 |
| PACEO(5)-6 | 10/90/100/10 | 6/94/100/10 | 20603 | 9642 | 2.14 |
| PACEO(5)-13 | 20/80/100/10 | 13/87/100/10 | 15963 | 7505 | 2.13 |
| PACEO(5)-20 | 30/70/100/10 | 20/80/100/10 | 13175 | 6463 | 2.04 |
| PACEO(5)-30 | 40/60/100/10 | 28/72/100/10 | 8767 | 4382 | 2.00 |
| PACEO(9)-8 | 10/90/100/10 | 8/92/100/10 | 18533 | 7097 | 2.6 |
| PACEO(9)-13 | 20/80/100/10 | 13/87/100/10 | 11187 | 5349 | 2.09 |
| PACEO(9)-20 | 30/70/100/10 | 20/80/100/10 | 9162 | 4799 | 1.91 |
| PACEO(9)-30 | 40/60/100/10 | 31/69/100/10 | 10092 | 5063 | 1.99 |
| PACEO(9)-35 | 50/50/100/10 | 35/65/100/10 | 8126 | 4290 | 1.89 |

*The PACEO(1) polymers have low molecular weight because the OEDE1 is less compatible with the enzyme, *Candida antartica* Lipase B (CALB)

The transfection efficiency of particles can be influenced by the structure and composition of the polymers. In some embodiments the structures of the ortho ester in the polymer modulate the transfection efficiency of the particles. In some embodiments the number of methylene groups defines structural differences within different polymers. The number of methylene groups is an integer within the range from 1-20, such as 1, 5 and 9.

In some embodiments the composition of the polymer is defined by the percent composition of the ortho esters. The percent composition of the ortho ester ranges from 1 to 99%. In some embodiments the percent composition of the ortho esters is 6%, 8%, 10%, 13%, 20%, 30%, 35%, 40%, and 50%.

As discussed in the Example below, the most preferred structure and composition of the polymer for efficient delivery of agents for a particular formulation can be determined empirically using the methods that are known in the art.

B. Therapeutic, Prophylactic or Diagnostic Agents

The agent to be delivered can be a small molecule agent (i.e., non-polymeric agent having a molecular weight less than 2,000, 1500, 1,000, 750, or 500 Dalton) or a macromolecule (e.g., an oligomer or polymer) such as proteins, enzymes, peptides, nucleic acids, etc. Suitable small molecule active agents include organic, inorganic, and/or organometallic compounds. The particles can be used for in vivo and/or in vitro delivery of the agent. Molecules other than genes can also be delivered. Since the polymer is very hydrophobic, it can bind with non-charged molecules through hydrophobic forces.

The polymers described herein can form various polymer compositions, which are useful for preparing a variety of biodegradable medical devices and for drug delivery. Devices prepared from the PHA copolymers described herein can be used for a wide range of different medical applications. Examples of such applications include controlled release of therapeutic, prophylactic or diagnostic agents; drug delivery; tissue engineering scaffolds; cell encapsulation; targeted delivery; biocompatible coatings; biocompatible implants; guided tissue regeneration; wound dressings; orthopedic devices; prosthetics and bone cements (including adhesives and/or structural fillers); and diagnostics.

The polymers described herein can be used to encapsulate, be mixed with, or be ionically or covalently coupled to any of a variety of therapeutic, prophylactic or diagnostic agents. A wide variety of biologically active materials can be encapsulated or incorporated, either for delivery to a site by the polymer, or to impart properties to the polymer, such as bioadhesion, cell attachment, enhancement of cell growth, inhibition of bacterial growth, and prevention of clot formation.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. The polymer can also be used to encapsulate cells and tissues. Representative diagnostic agents are agents detectable by x-ray, fluorescence, magnetic resonance imaging, radioactivity, ultrasound, computer tomography (CT) and positron emission tomography (PET). Ultrasound diagnostic agents are typically a gas such as air, oxygen or perfluorocarbons. In a preferred embodiment, the polymers are used for delivery of nucleic acids.

Exemplary therapeutic agents that can be incorporated into the particles include, but are not limited to, tumor antigens, CD4+ T-cell epitopes, cytokines, chemotherapeutic agents, radionuclides, small molecule signal transduction inhibitors, photothermal antennas, monoclonal antibodies, immunologic danger signaling molecules, other immunotherapeutics, enzymes, antibiotics, antivirals (especially protease inhibitors alone or in combination with nucleosides for treatment of HIV or Hepatitis B or C), anti-parasitics (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells), agents that promote uptake of the particles into cells (including dendritic cells and other antigen-presenting cells), nutraceuticals such as vitamins, and oligonucleotide drugs (including DNA, RNAs, antisense, aptamers, small interfering RNAs, ribozymes, external guide sequences for ribonuclease P, and triplex forming agents).

Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

Exemplary immunomodulatory agents include cytokines, xanthines, interleukins, interferons, oligodeoxynucleotides, glucans, growth factors (e.g., TNF, CSF, GM-CSF and G-CSF), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

Examples of immunological adjuvants that can be associated with the particles include, but are not limited to, TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives there of including, but not limited to, monophosphoryl lipid A (MPL), glycopyranosyl lipid A, PET-lipid A, and 3-O-desacyl-4'-monophosphoryl lipid A.

The particles may also include antigens and/or adjuvants (i.e., molecules enhancing an immune response). Peptide, protein, and DNA based vaccines may be used to induce immunity to various diseases or conditions. Cell-mediated immunity is needed to detect and destroy virus-infected cells. Most traditional vaccines (e.g. protein-based vaccines) can only induce humoral immunity. DNA-based vaccine represents a unique means to vaccinate against a virus or parasite because a DNA based vaccine can induce both humoral and cell-mediated immunity. In addition, DNA based vaccines are potentially safer than traditional vaccines. DNA vaccines are relatively more stable and more cost-effective for manufacturing and storage. DNA vaccines consist of two major components—DNA carriers (or delivery vehicles) and DNAs encoding antigens. DNA carriers protect DNA from degradation, and can facilitate DNA entry to specific tissues or cells and expression at an efficient level.

Exemplary diagnostic agents include paramagnetic molecules, fluorescent compounds, magnetic molecules, and radionuclides, x-ray imaging agents, and contrast agents.

Polynucleotides

The polynucleotide can encode one or more proteins, functional nucleic acids, or combinations thereof. The polynucleotide can be monocistronic or polycistronic. In some embodiments, the polynucleotide is multigenic. In some embodiments, the polynucleotide is transfected into the cell and remains extrachromosomal. In some embodiments, the polynucleotide is introduced into a host cell and is integrated into the host cell's genome. As discussed in more detail below, the compositions can be used in methods of gene therapy. Methods of gene therapy can include the introduction into the cell of a polynucleotide that alters the genotype of the cell. Introduction of the polynucleotide can correct, replace, or otherwise alter the endogenous gene via genetic recombination. Methods can include introduction of an entire replacement copy of a defective gene, a heterologous gene, or a small nucleic acid molecule such as an oligonucleotide. For example, a corrective gene can be introduced into a non-specific location within the host's genome.

In some embodiments, the polynucleotide is incorporated into or part of a vector. Methods to construct expression vectors containing genetic sequences and appropriate transcriptional and translational control elements are well known in the art. These methods include in vitro recombinant DNA techniques, synthetic techniques, and in vivo genetic recombination. Expression vectors generally contain regulatory sequences and necessary elements for the translation and/or transcription of the inserted coding sequence, which can be, for example, the polynucleotide of interest. The coding sequence can be operably linked to a promoter and/or enhancer to help control the expression of the desired gene product. Promoters used in biotechnology are of different types according to the intended type of control of gene expression. They can be generally divided into constitutive promoters, tissue-specific or development-stage-specific promoters, inducible promoters, and synthetic promoters.

For example, in some embodiments, the polynucleotide of interest is operably linked to a promoter or other regulatory elements known in the art. Thus, the polynucleotide can be a vector such as an expression vector. The engineering of polynucleotides for expression in a prokaryotic or eukaryotic system may be performed by techniques generally known to those of skill in recombinant expression. An expression vector typically comprises one of the disclosed compositions under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as $E.\ coli$ and $B.\ subtilis$ transformed with recombinant phage DNA, plasmid DNA or cosmid DNA expression vectors. It will be appreciated that any of these vectors may be packaged and delivered using the disclosed polymers.

Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the disclosed compositions. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

1. Polypeptide of Interest

The polynucleotide can encode one or more polypeptides of interest. The polypeptide can be any polypeptide. For example, the polypeptide encoded by the polynucleotide can be a polypeptide that provides a therapeutic or prophylactic effect to an organism or that can be used to diagnose a disease or disorder in an organism. For example, for treatment of cancer, autoimmune disorders, parasitic, viral, bacterial, fungal or other infections, the polynucleotide(s) to be expressed may encode a polypeptide that functions as a ligand or receptor for cells of the immune system, or can function to stimulate or inhibit the immune system of an organism. As discussed in the example below, a polynucleotide encoding TNF-related apoptosis-inducing ligand (TRAIL) can be delivered to tumor cells using the disclosed polyplexes in a method of treating cancer.

In some embodiments, the polynucleotide supplements or replaces a polynucleotide that is defective in the organism.

In some embodiments, the polynucleotide includes a selectable marker, for example, a selectable marker that is effective in a eukaryotic cell, such as a drug resistance selection marker. This selectable marker gene can encode a factor necessary for the survival or growth of transformed host cells grown in a selective culture medium. Typical selection genes encode proteins that confer resistance to antibiotics or other toxins, e.g., ampicillin, neomycin, methotrexate, kanamycin, gentamycin, Zeocin, or tetracycline, complement auxotrophic deficiencies, or supply critical nutrients withheld from the media.

In some embodiments, the polynucleotide includes a reporter gene. Reporter genes are typically genes that are not present or expressed in the host cell. The reporter gene typically encodes a protein which provides for some phenotypic change or enzymatic property. Examples of such genes are provided in Weising et al. *Ann. Rev. Genetics*, 22, 421 (1988). Preferred reporter genes include glucuronidase (GUS) gene and GFP genes.

2. Functional Nucleic Acids

The polynucleotide can be, or can encode a functional nucleic acid. Functional nucleic acids are nucleic acid molecules that have a specific function, such as binding a target molecule or catalyzing a specific reaction. Functional nucleic acid molecules can be divided into the following non-limiting categories: antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the polypeptide itself. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. There are numerous methods for optimization of antisense efficiency by finding the most accessible regions of the target molecule. Exemplary methods include in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $K_d$'s from the target molecule of less than $10^{-12}$ M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $k_d$ with the target molecule at least 10, 100, 1000, 10,000, or 100,000 fold lower than the $k_d$ with a background binding molecule. It is preferred when doing the comparison for a molecule such as a polypeptide, that the background molecule be a different polypeptide.

Ribozymes are nucleic acid molecules that are capable of catalyzing a chemical reaction, either intramolecularly or intermolecularly. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

Triplex forming functional nucleic acid molecules are molecules that can interact with either double-stranded or single-stranded nucleic acid. When triplex molecules interact with a target region, a structure called a triplex is formed in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$.

External guide sequences (EGSs) are molecules that bind a target nucleic acid molecule forming a complex, which is recognized by RNase P, which then cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukaryotic cells. Representative examples of how to make and use EGS molecules to facilitate cleavage of a variety of different target molecules are known in the art.

Gene expression can also be effectively silenced in a highly specific manner through RNA interference (RNAi). This silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, et al. (2001) Genes Dev., 15:188-200; Bernstein, et al. (2001) Nature, 409:363-6; Hammond, et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, et al. (2001) Nature, 411:494 498) (Ui-Tei, et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAse (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors.

3. Composition of the Polynucleotides

The polynucleotide can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose sugar linked by phosphodiester bonds.

The polynucleotide can be composed of nucleotide analogs that have been chemically modified to improve stability, half-life, or specificity or affinity for a target sequence, relative to a DNA or RNA counterpart. The chemical modifications include chemical modification of nucleobases, sugar moieties, nucleotide linkages, or combinations thereof. As used herein "modified nucleotide" or "chemically modified nucleotide" defines a nucleotide that has a chemical modification of one or more of the heterocyclic base, sugar moiety or phosphate moiety constituents. In some embodiments, the charge of the modified nucleotide is reduced compared to DNA or RNA oligonucleotides of the same nucleobase sequence. For example, the oligonucleotide can have low negative charge, no charge, or positive charge. Modifications should not prevent, and preferably enhance, the ability of the oligonucleotides to enter a cell and carry out a function such inhibition of gene expression as discussed above.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

As discussed in more detail below, in one preferred embodiment, the oligonucleotide is a morpholino oligonucleotide.

a. Heterocyclic Bases

The principal naturally-occurring nucleotides include uracil, thymine, cytosine, adenine and guanine as the heterocyclic bases. The oligonucleotides can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-.beta.-D-ribofuranosyl)pyridine (2-aminopyridine), and various pyrrolo- and pyrazolopyrimidine derivatives.

b. Sugar Modifications Polynucleotides can also contain nucleotides with modified sugar moieties or sugar moiety analogs. Sugar moiety modifications include, but are not limited to, 2'-O-aminoetoxy, 2'-O-amonioethyl (2'-OAE), 2'-O-methoxy, 2'-O-methyl, 2-guanidoethyl (2'-OGE), 2'-O, 4'-C-methylene (LNA), 2'-O-(methoxyethyl) (2'-OME) and 2'-O—(N-(methyl)acetamido) (2'-OMA). 2'-O-aminoethyl sugar moiety substitutions are especially preferred because they are protonated at neutral pH and thus suppress the charge repulsion between the TFO and the target duplex. This modification stabilizes the C3'-endo conformation of the ribose or dexyribose and also forms a bridge with the i−1 phosphate in the purine strand of the duplex.

The polynucleotide can be a morpholino oligonucleotide. Morpholino oligonucleotides are typically composed of two more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of an oligomer:RNA heteroduplex to resist RNAse degradation. In some embodiments, oligonucleotides employ morpholino-based subunits bearing base-pairing moieties, joined by uncharged linkages.

c. Internucleotide Linkages

Internucleotide bond refers to a chemical linkage between two nucleoside moieties. Modifications to the phosphate backbone of DNA or RNA oligonucleotides may increase the binding affinity or stability polynucleotides, or reduce the susceptibility of polynucleotides to nuclease digestion. Cationic modifications, including, but not limited to, diethyl-ethylenediamide (DEED) or dimethyl-aminopropylamine (DMAP) may be especially useful due to decrease electrostatic repulsion between the oligonucleotide and a target. Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable in vivo.

Examples of modified nucleotides with reduced charge include modified internucleotide linkages such as phosphate analogs having achiral and uncharged intersubunit linkages (e.g., Sterchak, et al., Organic Chem., 52:4202, (1987)), and uncharged morpholino-based polymers having achiral intersubunit linkages (see, e.g., U.S. Pat. No. 5,034,506), as discussed above. Some internucleotide linkage analogs include morpholidate, acetal, and polyamide-linked heterocycles.

In another embodiment, the oligonucleotides are composed of locked nucleic acids. Locked nucleic acids (LNA) are modified RNA nucleotides (see, for example, Braasch, et al., Chem. Biol., 8(1):1-7 (2001)). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the oligonucleotides are composed of peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are comprised of peptide nucleic acid monomers.

Other backbone modifications include peptide and amino acid variations and modifications. Thus, the backbone constituents of oligonucleotides such as PNA may be peptide linkages, or alternatively, they may be non-peptide peptide linkages. Examples include acetyl caps, amino spacers such as 8-amino-3,6-dioxaoctanoic acid (referred to herein as O-linkers), amino acids such as lysine are particularly useful if positive charges are desired in the PNA. Methods for the chemical assembly of PNAs are well known. See, for example, U.S. Pat. Nos. 5,539,082, 5,527,675, 5,623,049, 5,714,331, 5,736,336, 5,773,571, and 5,786,571.

Polynucleotides optionally include one or more terminal residues or modifications at either or both termini to increase stability, and/or affinity of the oligonucleotide for its target. Commonly used positively charged moieties include the amino acids lysine and arginine, although other positively charged moieties may also be useful. For example, lysine and arginine residues can be added to a bis-PNA linker or can be added to the carboxy or the N-terminus of a PNA strand. Polynucleotides may further be modified to be end capped to prevent degradation using a 3' propylamine group. Procedures for 3' or 5' capping oligonucleotides are well known in the art.

C. Nano and Microparticles and Micelles

Polyplex with liquid polymers can be encapsulated within particles or non-covalently associated with the surface of particles. For solid polymers, the polyplex is dispersed within the polymer matrix.

1. Particles

The polymers described above can be used to prepare micro- and/or nanoparticles having encapsulated therein one or more therapeutic, diagnostic, or prophylactic agents. The agent can be encapsulated within the particle, dispersed within the polymer matrix that forms the particle, covalently or non-covalently associated with the surface of the particle or combinations thereof.

D. Size of Polyplexes and Methods of Reducing Aggregation

Resistance to aggregation can be important because maintaining a small particle size limits clearance by the liver and maintains transfection ability of polyplex particles into target cells. Therefore, in preferred embodiments, the polyplexes are resistant to aggregation. Preferably, polyplexes with or without coating are between about 1 nm and 1000 nm in radius, more preferably between about 1 nm and about 500 nm in radius, most preferably between about 15 nm and about 250 nm in radius. In some embodiments, coated polyplexes loaded with polynucleotide are between about 150 nm and 275 nm in radius.

The ratio of polynucleotide weight to polymer weight (polynucleotide:polymer), the content and quantity of polyplex coating, or a combination thereof can be used to adjust the size of the polyplexes.

In some embodiments, transfection efficiency of particles with 25:1 polymer to DNA ratio is lower than the transfection efficiency of particles with 50:1, 100:1, 150:1, and 200:1 polymer:DNA ratios. The most preferred polymer:polynucleotide ratio for a particular formulation can be determined empirically using the methods that are known in the art. Generally, the weight:weight ratio of polymer:polynucleotide is preferably greater than about 10:1, more preferably greater than about 50:1, most preferably greater than about 100:1. The weight:weight ratio of polymer:polynucleotide is preferably between about 10:1 and 500:1, more preferably between about 25:1 and 250:1, most preferably between about 50:1 and 150:1. In some embodiments, the weight ratio of polymer:polynucleotide is about 100:1. Preferably, the polyplexes has are spherical in shape.

In some embodiments, transfection efficiency of particles is influenced by the ratio of coating agent molecules to polynucleotide molecules (coating agent:polynucleotide). The ratio is expressed by weight. The most preferred coating agent:polynucleotide ratio for a particular formulation can be determined empirically using the methods that are known in the art. Generally, the ratio of coating agent:polynucleotide is greater than 0, and preferably lower than about 50:1, more preferably lower than about 25:1, most preferably lower than about 10:1. The ratio coating agent:polynucleotide is preferably between about 1:1 and 10:1, more preferably between about 2.5:1 and 7.5:1. In some embodiments, the ratio of coating agent:polynucleotide is about 5:1. Ratios of coating agent:polynucleotide of 10:1, 5:1, and 2.5:1 are also referred to herein as 10×, 5×, and 2.5× respectively. Preferably, the polyplexes are spherical in shape.

In some embodiments, particles produced using the methods described here in contain less than 80%, less then 75%, less than 70%, less than 60%, less than 50% by weight, less than 40% by weight, less than 30% by weight, less than 20% by weight, less than 15% by weight, less than 10% by weight, less than 5% by weight, less than 1% by weight, less than 0.5% by weight, or less than 0.1% by weight of the agent. In some embodiments, the agent may be a mixture of pharmaceutically active agents. The percent loading is dependent on a variety of factors, including the agent to be encapsulated, the polymer used to prepare the particles, and/or the method used to prepare the particles.

The particles may provide controlled release of the drug. For example, the unaltered particles may provide release of an effective amount of the drug over time based on the rate of diffusion of the drug form the particle and/or the rate of degradation of the polymer. The polymer composition can be varied to manipulate the degradation behavior of the polymer and thus the release rate/time of the agent to be delivered. Alternatively, the particle can be coated with one or more materials to provide controlled release, such as sustained release or delayed release of the agent or agents to be delivered.

Sustained release and delayed release materials are well known in the art. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water-soluble protein can be spray coated onto the microparticles and subsequently cross-linked by the one of the methods described above. Alternatively, drug-containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

Controlled release polymers known in the art include acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename EUDRAGIT®. In further preferred embodiments, the acrylic polymer comprises a mixture of two acrylic resin lacquers commercially available from Rohm Pharma under the tradenames EUDRAGIT® RL30D and EUDRAGIT® RS30D, respectively. EUDRAGIT® RL30D and EUDRAGIT® RS30D are copolymers of acrylic and methacrylic esters with a low content of quaternary ammonium groups, the molar ratio of ammonium groups to the remaining neutral (meth)acrylic esters being 1:20 in EUDRAGIT® RL30D and 1:40 in EUDRAGIT® RS30D. The mean molecular weight is about 150,000. EUDRAGIT® S-100 and EUDRAGIT® L-100 are also preferred. The code designations RL (high permeability) and RS (low permeability) refer to the permeability properties of these agents. EUDRAGIT® RL/RS mixtures are insoluble in water and in digestive fluids. However, multiparticulate systems formed to include the same are swellable and permeable in aqueous solutions and digestive fluids.

The polymers described above such as EUDRAGIT® RL/RS may be mixed together in any desired ratio in order to ultimately obtain a sustained-release formulation having a desirable dissolution profile. Desirable sustained-release multiparticulate systems may be obtained, for instance, from 100% EUDRAGIT®RL, 50% EUDRAGIT®RL and 50% EUDRAGIT® RS, and 10% EUDRAGIT® RL and 90% EUDRAGIT®RS. One skilled in the art will recognize that other acrylic polymers may also be used, such as, for example, EUDRAGIT®L.

Other controlled release materials include methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and CARBOPOL® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT® (Rohm Pharma; Westerstadt, Germany), including EUDRAGIT® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGITS® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac.

1. Micelles

The polymers described herein, such as the quaterpolymers or PEG-block containing polymers can be used to prepare micelles. The average micelle size is typically in the range from about 100 to about 500 nm, preferably from about 100 to about 400 nm, more preferably from about 100 to about 300 nm, more preferably from about 150 to about 200 nm, most preferably from about 160 to about 190 nm, which were stable at physiological pH of 7.4 in the presence of serum proteins. The copolymers possess high blood compatibility and exhibit minimal activity to induce hemolysis and agglutination.

The size and zeta potential of the micelles were found to change significantly when the pH of the aqueous medium accommodating the micelles was varied. This pH-responsive behavior for the micelles is anticipated since cores of the micelles become protonated at low pH and become more hydrophilic, thus absorbing more water molecules from the aqueous medium to cause swelling of the micelles. The ortho ester content can also affect the magnitude of the micelle size at different pH values. Decreasing the ortho ester content and increasing tertiary amino group content in the polymer, increases the capacity of the micelle cores to absorb protons and water molecules, thereby increasing the micelle size.

The zeta potential of the micelles in aqueous medium can also exhibit pH-dependence. The surface charge dependence on pH can be attributed to the protonation or deprotonation of the cores of the micelles at different medium pH. At an alkaline pH (7.4-8.5), most of the amino groups in the micelles presumably are not protonated, and the micelle particles remain negatively charged due to the absorption of $HPO_4^{2-}$ and/or $H_2PO_4^-$ anions in PBS by the micelles. Upon decreasing pH from 7.4 to 5.0, the tertiary amino moieties in the micelle cores become mostly protonated, turning the micelles to positively charged particles. The micelle surface charge responses to the medium pH are highly desirable since the negative surface charge of the micelles at physiological pH can alleviate the interaction of the micelles with serum protein in the blood and prolong their in vivo circulation time. On the other hand, the reverse to positive surface charge at the tumor extracellular pH of approximately 6.5 could enhance the uptake of these micelles by target tumor cells.

It is known that nanoparticles with nearly neutral surface charge (zeta potential between −10 and +10 mV) can decrease their uptake by the reticuloendothelial system (RES) and prolong their circulation time in the blood. The negative surface charges of the micelles could result from the absorption of $HPO_4^{2-}$ and/or $H_2PO_4^-$ anions in PBS by the micelle particles via hydrogen bonding interactions between the anions and the ether groups of PEG shells or the amino groups of the cores. For amphiphilic block copolymer micelles, it is anticipated that hydrophilic chain segments (e.g., PEG) in the outer shell of the micelles can shield the charges in the micelle core with the long chain blocks being more effective in reducing zeta potential than the short chain blocks.

The polymer micelles are pH-responsive: decreasing the medium pH from 7.4 to 4.0, reduced the residual polymer content in a PBS buffer. This phenomenon can be exploited to improve release of agents at tumor sites, since it is known that the tumor microenvironment is typically weakly acidic (e.g., 5.7-7.0) as the result of lactic acid accumulation due to poor oxygen perfusion. In contrast, the extracellular pH of the normal tissue and blood is slightly basic (pH of 7.2-7.4). Thus, enhanced drug delivery efficiency is anticipated for anticancer drug-loaded micelles that are pH-responsive and can be triggered by acidic pH to accelerate the drug release. Furthermore, even more acidic conditions (pH=4.0-6.0) are encountered in endosomes and lysosomes after uptake of the micelles by tumor cells via endocytosis pathways, which may further increase the cytotoxicity of the drug-encapsulated micelles.

E. Coating Agents for Polyplexes

Efficiency of polynucleotide delivery using the disclosed polymers can be affected by the positive charges on the polyplex surface. For example, a zeta potential of the polyplex of +8.9 mV can attract and bind with negatively charged plasma proteins in the blood during circulation and lead to rapid clearance by the reticuloendothelial system (RES). In some embodiments the polyplexes are treated or coated to improve polynucleotide delivery efficiency. In some embodiments, the coating improves cell specific targeting of the polyplex, improves the stability (i.e., stabilizes the size of the polyplex in vivo), increases the half-life of the polyplex in vivo (i.e., in systemic circulation), or combinations thereof compared to a control. In some embodiments, the control is a polyplex without a coating.

1. Compositions for Altering Surface Charge

Polynucleotide delivery efficiency of the disclosed polyplexes can be improved by coating the particles with an agent that is negatively charged at physiological pH. Preferably, the negatively charged agent is capable of electrostatic binding to the positively charged surface of the polyplexes. The negatively charged agent can neutralize the charge of the polyplex, or reverse the charge of the polyplex. In some embodiments, the negatively charged agent imparts a net negative charge to the polyplex.

In some embodiments, the negatively charged agent is a negatively charged polypeptide. For example, the polypeptide can include aspartic acids, glutamic acids, or a combination therefore, such that the overall charge of the polypeptide is a negative at neutral pH. In some embodiments, the polypeptide is a poly aspartic acid polypeptide consisting of 3, 4, 5, 6, 7, 8, 9, 10, 11, 12, 13, 14, 15, 16, 17, 18, 19, 20, or more than 20 aspartic acid residues. In some embodiments, the polypeptide is a poly glutamic acid polypeptide consisting of 3, 4, 5, 6, 7, 8, 9, 10, 11, 12, 13, 14, 15, 16, 17, 18, 19, 20, or more than 20 glutamic acid residues. Other negatively charged molecules include small molecules (i.e., MW less than 1500, 100, 750, or 500 Daltons) such as hyaluronic acid.

Increasing the negative charge on the surface of the particle can reduce or prevent the negative interactions described above, wherein more positively charged particles attract and bind negatively charged plasma proteins in the blood during circulation and lead to rapid clearance by the reticuloendothelial system (RES). In some embodiments, the zeta potential of the particles is from about −15 mV to about 10 mV, preferably from about −15 mV to about 8 mV, more preferably from about −10 mV to about 8 mV, more preferably from about −8 mV to about 8 mV. The zeta potential can be more negative or more positive than the ranges above provided the particles are stable (i.e., do not aggregate, etc.) and not readily cleared from the blood stream. The zeta potential can be manipulated by coating or functionalizing the particle surface with one or more moieties that vary the surface charge. Alternatively, the monomers themselves can be functionalized and/or additional monomers can be introduced into the polymer, which vary the surface charge.

2. Linkers

In some embodiments the polyplex can be coated with both a negatively charged agent and a targeting moiety. In some embodiments, the negatively charged agent and the targeting moiety are linked together by a linker. The linker can be a polypeptide, or any other suitable linker that is known in the art, for example, poly ethylene glycol (PEG).

In some embodiments, the linker is polypeptide that has approximately neutral charge at physiological pH. In some embodiments, the linker polypeptide is a polyglycine. For example, in some embodiments the linker consists of 3, 4, 5, 6, 7, 8, 9, 10, 11, 12, 13, 14, 15, 16, 17, 18, 19, 20, or glycine residues. In a preferred embodiment, the linker is a 6-residue polyglycine.

In some embodiments, the negatively charged agent alone, or in combination with a targeting moiety is linked to the polyplex by electrostatic interactions. In some embodiments, the negative charged agent, the targeting moiety, or a combination thereof is linked to the polyplex by covalent conjugation to the polymer backbone or to a side chain attached to the polymer backbone.

3. Targeting Moieties

In some embodiments, the polyplexes include a cell-type or cell-state specific targeting domain or targeting signal. Examples of moieties which may be linked or unlinked to the polyplexes include, for example, targeting moieties which provide for the delivery of molecules to specific cells. The targeting signal or sequence can be specific for a host, tissue, organ, cell, organelle, non-nuclear organelle, or cellular compartment. For example, the compositions disclosed herein can be modified with galactosyl-terminating macromolecules to target the compositions to the liver or to liver cells. The modified compositions selectively enter hepatocytes after interaction of the carrier galactose residues with the asialoglycoprotein receptor present in large amounts and high affinity only on these cells. Moreover, the compositions disclosed here can be targeted to other specific intercellular regions, compartments, or cell types.

In one embodiment, the targeting signal binds to its ligand or receptor which is located on the surface of a target cell such as to bring the vector and cell membranes sufficiently close to each other to allow penetration of the vector into the cell. Additional embodiments of the present disclosure are directed to specifically delivering polynucleotides to specific tissue or cell types, wherein the polynucleotides can encode a polypeptide or interfere with the expression of a different polynucleotide. The polynucleotides delivered to the cell can encode polypeptides that can enhance or contribute to the functioning of the cell.

The targeting moiety can be an antibody or antigen binding fragment thereof, an antibody domain, an antigen, a T-cell receptor, a cell surface receptor, a cell surface adhesion molecule, a major histocompatibility locus protein, a viral envelope protein and a peptide selected by phage display that binds specifically to a defined cell.

One skilled in the art will appreciate that the tropism of the polyplexes described can be altered by merely changing the targeting signal. It is known in the art that nearly every cell type in a tissue in a mammalian organism possesses some unique cell surface receptor or antigen. Thus, it is possible to incorporate nearly any ligand for the cell surface receptor or antigen as a targeting signal. For example, peptidyl hormones can be used a targeting moieties to target delivery to those cells which possess receptors for such hormones. Chemokines and cytokines can similarly be employed as targeting signals to target delivery of the complex to their target cells. A variety of technologies have been developed to identify genes that are preferentially expressed in certain cells or cell states and one of skill in the art can employ such technology to identify targeting signals which are preferentially or uniquely expressed on the target tissue of interest.

Tumor Targeting

In one embodiment, the targeting signal is used to selectively target tumor cells. Tumor cells express cell surface markers which may only be expressed in the tumor or present in non-tumor cells but preferentially presented in tumor cells. Such markers can be targeted to increase delivery of the polyplexes to cancer cells.

For example, in some embodiments, the targeting moiety is a polypeptide including an arginine-glycine-aspartic acid sequence. For example, the targeting moiety can be an arginine-glycine-aspartic acid-lysine (RGDK, mRGD) other polypeptide that includes the RGD sequence and is capable of binding to tumor endothelium through the interaction of RGD with $\alpha_v\beta_3$ and $\alpha_v\beta_5$. In some embodiments, a targeting moiety includes the polypeptide sequence R/KxxR/K, where "x" is any amino acid, and which allows binding to neuropilin-1. Binding with integrins or neuropilin-1 are two approaches for improving tumor-targeted and tissue-penetrating delivery to tumors in vivo. Similar approaches have been reported to facilitate ligand-specific gene delivery in vitro and targeted gene delivery to liver, spleen, and bone marrow in vivo.

Other, exemplary tumor specific cell surface markers include, but are not limited to, alfa-fetoprotein (AFP), C-reactive protein (CRP), cancer antigen-50 (CA-50), cancer antigen-125 (CA-125) associated with ovarian cancer, cancer antigen 15-3 (CA15-3) associated with breast cancer, cancer antigen-19 (CA-19) and cancer antigen-242 associated with gastrointestinal cancers, carcinoembryonic antigen (CEA), carcinoma associated antigen (CAA), chromogranin A, epithelial mucin antigen (MC5), human epithelium specific antigen (HEA), Lewis(a)antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdr1 gene product), multidrug-resistance-related antigen, p170, multidrug-resistance-related antigen, prostate specific antigen (PSA), CD56, NCAM, EGFR, CD44, and folate receptor. In one embodiment, the targeting signal consists of antibodies which are specific to the tumor cell surface markers.

Antibodies

Another embodiment provides an antibody or antigen binding fragment thereof bound to the disclosed polyplex acts as the targeting signal. The antibodies or antigen binding fragment thereof are useful for directing the polyplex to a cell type or cell state. In one embodiment, the polyplex is coated with a polypeptide that is an antibody binding domain, for example from a protein known to bind antibodies such as Protein A and Protein G from *Staphylococcus aureus*. Other domains known to bind antibodies are known in the art and can be substituted. The antibody binding domain links the antibody, or antigen binding fragment thereof, to the polyplex.

In certain embodiments, the antibody that serves as the targeting signal is polyclonal, monoclonal, linear, humanized, chimeric or a fragment thereof. Representative antibody fragments are those fragments that bind the antibody binding portion of the non-viral vector and include Fab, Fab', F(ab'), Fv diabodies, linear antibodies, single chain antibodies and bispecific antibodies known in the art.

In some embodiments, the targeting signal includes all or part of an antibody that directs the polyplex to the desired target cell type or cell state. Antibodies can be monoclonal or polyclonal, but are preferably monoclonal. For human gene therapy purposes, antibodies can be derived from human genes and are specific for cell surface markers, and are produced to reduce potential immunogenicity to a human host as is known in the art. For example, transgenic mice which contain the entire human immunoglobulin gene cluster are capable of producing "human" antibodies can be utilized. In one embodiment, fragments of such human antibodies are employed as targeting signals. In a preferred embodiment, single chain antibodies modeled on human antibodies are prepared in prokaryotic culture.

Brain Targeting

In one embodiment, the targeting signal is directed to cells of the nervous system, including the brain and peripheral nervous system. Cells in the brain include several types and states and possess unique cell surface molecules specific for the type. Furthermore, cell types and states can be further characterized and grouped by the presentation of common cell surface molecules.

In one embodiment, the targeting signal is directed to specific neurotransmitter receptors expressed on the surface of cells of the nervous system. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter or ligand capable of specifically binding to a neurotransmitter receptor.

In one embodiment, the targeting signal is specific to cells of the nervous system which may include astrocytes, microglia, neurons, oligodendrites and Schwann cells. These cells can be further divided by their function, location, shape, neurotransmitter class and pathological state. Cells of the nervous system can also be identified by their state of differentiation, for example stem cells Exemplary markers specific for these cell types and states are well known in the art and include, but are not limited to CD133 and Neuro sphere.

Muscle Targeting

In one embodiment, the targeting signal is directed to cells of the musculoskeletal system. Muscle cells include several types and possess unique cell surface molecules specific for the type and state. Furthermore, cell types and states can be further characterized and grouped by the presentation of common cell surface molecules.

In one embodiment, the targeting signal is directed to specific neurotransmitter receptors expressed on the surface of muscle cells. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter. Exemplary neurotransmitters expressed on muscle cells that can be targeted include but are not limited to acetycholine and norepinephrine.

In one embodiment, the targeting signal is specific to muscle cells which consist of two major groupings, Type I and Type II. These cells can be further divided by their function, location, shape, myoglobin content and pathological state. Muscle cells can also be identified by their state of differentiation, for example muscle stem cells. Exemplary markers specific for these cell types and states are well known in the art include, but are not limited to MyoD, Pax7, and MR4.

An exemplary polyplex coating for targeting tumor cells is polyE-mRGD. As used herein, polyE-mRGD refers to a synthetic peptide containing three segments: a first segment including a polyglutamic acid (polyE) stretch, which is negatively charged at physiological pH and, therefore, capable of electrostatic binding to the positively charged surface of the polyplexes; a second segment including a neutral polyglycine stretch, which serves as a neutral linker; and a third segment that includes a RGD sequence that binds the tumor endothelium through the interaction of RGD with $\alpha_v\beta_3$ and $\alpha_v\beta_5$.

In one embodiment, polyE-mRGD includes the sequence EEEEEEEEEEEEEEEEGGGGGGRGDK (SEQ ID NO:1), or RGDKGGGGGG EEEEEEEEEEEEEEE (SEQ ID NO:2), or a variant thereof with 85%, 90%, 95%, or more than 95% sequence identity to SEQ ID NO:1 or 2.

Another exemplary coating that can be used to prepare charge neutral, or negatively charged particles that maintain their size in vivo are described in Harris, et al., *Biomaterials*, 31:998-1006 (2010)), and can include the amino acid sequence GGGGGGEEEEEEEEEEEEEEEE (SEQ ID NO:3, poly-E), for non-specific systemic administration, or the amino acids sequence GdPdLGdVdRG-GGGGGG-EE-EEEEEEEEEEEEEE-CONH2 (SEQ ID NO:4, poly-E-cat), which contains a polycationic sequence that increase targeting to the spleen, spine, sternum, and femur. In some embodiments, the polypeptide used in the coating is a variant SEQ ID NO:3 or 4, with 85%, 90%, 95%, or more than 95% sequence identity to SEQ ID NO:3 or 4.

In vitro studies have indicated that adsorption of immunoglobulin G (IgG) and complement protein C3 to nanoparticles increases their uptake by Kupffer cells and incubation in serum increases hepatic uptake in vivo following liver perfusion (Nagayama, et al., *Int. J. Pharm.*, 342:215-21 (2007)). Reports also indicate that galactose can be used to guide polymeric gene delivery particles to hepatocytes via the asialoglycoprotein receptor (ASGPR (SEQ ID NO:6) (Zhang, et al., *J. Controlled Release*, 102:749-63 (2005)).

F. Formulations

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, desintegrators, fillers, and coating compositions.

The particles are useful in drug delivery (as used herein "drug" includes therapeutic, nutritional, diagnostic and prophylactic agents), whether injected intravenously, subcutaneously, or intramuscularly, administered to the nasal or pulmonary system, injected into a tumor milieu, or administered to a mucosal surface (vaginal, rectal, buccal, sublingual). The particles may be administered as a dry powder, as an aqueous suspension (in water, saline, buffered saline, etc), in a hydrogel, organogel, or liposome, in capsules, tablets, troches, or other standard pharmaceutical excipient.

In some embodiments, the compositions are administered systemically, for example, by intravenous or intraperitoneal administration, in an amount effective for delivery of the compositions to targeted cells. Other possible routes include trans-dermal or oral.

In certain embodiments, the compositions are administered locally, for example by injection directly into a site to be treated. In some embodiments, the compositions are injected or otherwise administered directly to one or more tumors. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., Drug Delivery Systems (Chichester, England: Ellis Horwood Ltd., 1987), which can effect a sustained release of the polyplexes to the immediate area of the implant.

The polyplexes can be provided to the cell either directly, such as by contacting it with the cell, or indirectly, such as through the action of any biological process. For example, the polyplexes can be formulated in a physiologically acceptable carrier or vehicle, and injected into a tissue or fluid surrounding the cell. The polyplexes can cross the cell membrane by simple diffusion, endocytosis, or by any active or passive transport mechanism.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower. Generally, the total amount of the polyplex-associated nucleic acid administered to an individual will be less than the amount of the unassociated nucleic acid that must be administered for the same desired or intended effect.

In a preferred embodiment the polyplexes are administered in an aqueous solution, by parenteral injection. As discussed in the Examples below, in some embodiments, a formulation suitable for systemic administration by injection includes glucose.

The formulation can be in the form of a suspension or emulsion. In general, pharmaceutical compositions are provided including effective amounts of nucleic acids optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized for, for example, filtration through a bacteria retaining filter, by incorporating sterilizing agents into the compositions, by irradiating the compositions, or by heating the compositions.

The polyplexes can be applied topically. Topical administration can include application to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the ULTRAVENT® nebulizer (Mallinckrodt Inc., St. Louis, Mo.); the ACORN® II nebulizer (Marquest Medical Products, Englewood, Colo.); the VENTOLIN® metered dose inhaler (Glaxo Inc., Research Triangle Park, N.C.); and the SPINHALER® powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the formulation may also contain minor amount of nontoxic auxiliary substances such as wetting or emulsifying agents, dyes, pH buffering agents, and preservatives.

Exemplary methods of preparing polyplexes for transfection are discussed in the Examples below.

II. Methods for Making Particles

As noted above, the polyplexes can be dispersed in, encapsulated by or otherwise associated with polymeric particles. Particles can be prepared using a variety of techniques known in the art. The technique to be used can depend on a variety of factors including the polymer used to form the nanoparticles, the desired size range of the resulting particles, and suitability for the material to be encapsulated. Suitable techniques include, but are not limited to:

a. Solvent Diffusion/Displacement.

In this method, water-soluble or water-miscible organic solvents are used to dissolve the polymer and form emulsion upon mixing with the aqueous phase. The quick diffusion of the organic solvent into water leads to the formation of nanoparticles immediately after the mixing.

b. Solvent Evaporation.

In this method the polymer is dissolved in a volatile organic solvent. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid nanoparticles. The resulting nanoparticles are washed with water and dried overnight in a lyophilizer. Nanoparticles with different sizes and morphologies can be obtained by this method.

c. Hot Melt Microencapsulation.

In this method, the polymer is first melted and then mixed with the solid particles. The mixture is suspended in a non-miscible solvent (like silicon oil), and, with continuous stirring, heated to 5° C. above the melting point of the polymer. Once the emulsion is stabilized, it is cooled until the polymer particles solidify. The resulting nanoparticles are washed by decantation with petroleum ether to give a free-flowing powder. The external surfaces of spheres prepared with this technique are usually smooth and dense.

d. Solvent Removal.

In this method, the drug is dispersed or dissolved in a solution of the selected polymer in a volatile organic solvent. This mixture is suspended by stirring in an organic oil (such as silicon oil) to form an emulsion. Unlike solvent evaporation, this method can be used to make nanoparticles from polymers with high melting points and different molecular weights. The external morphology of spheres produced with this technique is highly dependent on the type of polymer used.

e. Spray-Drying.

In this method, the polymer is dissolved in organic solvent. A known amount of the active drug is suspended (insoluble drugs) or co-dissolved (soluble drugs) in the polymer solution. The solution or the dispersion is then spray-dried.

f. Phase Inversion.

Nanospheres can be formed from polymers using a phase inversion method wherein a polymer is dissolved in a "good" solvent, fine particles of a substance to be incorporated, such as a drug, are mixed or dissolved in the polymer solution, and the mixture is poured into a strong non solvent for the polymer, to spontaneously produce, under favorable conditions, polymeric microspheres, wherein the polymer is either coated with the particles or the particles are dispersed in the polymer. The method can be used to produce nanoparticles in a wide range of sizes, including, for example, about 100 nanometers to about 10 microns. Substances which can be incorporated include, for example, imaging agents such as fluorescent dyes, or biologically active molecules such as proteins or nucleic acids. In the process, the polymer is dissolved in an organic solvent and then contacted with a non solvent, which causes phase inversion of the dissolved polymer to form small spherical particles, with a narrow size distribution optionally incorporating an antigen or other substance.

g. Other Methods of Forming Particles

Other methods known in the art that can be used to prepare nanoparticles include, but are not limited to, polyelectrolyte condensation (see Suk et al., *Biomaterials*, 27, 5143-5150 (2006)); single and double emulsion (probe sonication); nanoparticle molding, and electrostatic self-assembly (e.g., polyethylene imine-DNA or liposome).

In one embodiment, the loaded particles are prepared by combining a solution of the polymer, typically in an organic solvent, with the polynucleotide of interest. The polymer solution is prepared by dissolving or suspending the polymer in a solvent. The solvent should be selected so that it does not adversely effect (e.g., destabilize or degrade) the nucleic acid to be encapsulated. Suitable solvents include, but are not limited to DMSO and methylene chloride. The concentration of the polymer in the solvent can be varied as needed. In some embodiments, the concentration is for example 25 mg/ml. The polymer solution can also be diluted in a buffer, for example, sodium acetate buffer.

Next, the polymer solution is mixed with the agent to be encapsulated, such as a polynucleotide. The agent can be dissolved in a solvent to form a solution before combining it with the polymer solution. In some embodiments, the agent is dissolved in a physiological buffer before combining it with the polymer solution. The ratio of polymer solution volume to agent solution volume can be 1:1. The combination of polymer and agent are typically incubated for a few minutes to form particles before using the solution for its desired purpose, such as transfection. For example, a polymer/polynucleotide solution can be incubated for 2, 5, 10, or more than 10 minutes before using the solution for transfection. The incubation can be at room temperature.

In some embodiments, the particles are also incubated with a solution containing a coating agent prior to use. The particle solution can be incubated with the coating agent for 2, 5, 10, or more than 10 minutes before using the polyplexes for transfection. The incubation can be at room temperature.

In these polymers, the charged group is tertiary amine, which is different from the classic concept of polycation, which is more like salt which gets charged by dissolving the anion in water. In essence, the tertiary amine groups in the methyl diethanolamine is protonated under acidic conditions to become a cation. Several protonated tertiary amine groups give rise to the polycationic character.

In some embodiments, if the agent is a polynucleotide, the polynucleotide is first complexed to a polycation before mixing with polymer. Complexation can be achieved by mixing the polynucleotides and polycations at an appropriate molar ratio. When a polyamine is used as the polycation species, it is useful to determine the molar ratio of the polyamine nitrogen to the polynucleotide phosphate (N/P ratio). In a preferred embodiment, inhibitory RNAs and polyamines are mixed together to form a complex at an N/P ratio of between approximately 1:1 to 1:25, preferably between about 8:1 to 15:1. The volume of polyamine solution required to achieve particular molar ratios can be determined according to the following formula:

$$V_{NH2} = \frac{C_{inhRNA,final} \times M_{w,inhRNA} / C_{inhRNA,final} \times M_{w,P} \times \Phi_{N:P} \times \Phi V_{final}}{C_{NH2}/M_{w,NH2}}$$

where $M_{w,inhRNA}$=molecular weight of inhibitory RNA, $M_{w,P}$=molecular weight of phosphate groups of inhibitory RNA, $\Phi_{N:P}$=N:P ratio (molar ratio of nitrogens from polyamine to the ratio of phosphates from the inhibitory RNA), $C_{NH2}$, stock=concentration of polyamine stock solution, and $M_{w,NH2}$=molecular weight per nitrogen of polyamine. Methods of mixing polynucleotides with polycations to condense the polynucleotide are known in the art. See for example U.S. Published Application No. 2011/0008451.

The term "polycation" refers to a compound having a positive charge, preferably at least 2 positive charges, at a selected pH, preferably physiological pH. Polycationic moieties have between about 2 to about 15 positive charges, preferably between about 2 to about 12 positive charges, and more preferably between about 2 to about 8 positive charges at selected pH values. Many polycations are known in the art. Suitable constituents of polycations include basic amino acids and their derivatives such as arginine, asparagine, glutamine, lysine and histidine; cationic dendrimers; and amino polysaccharides. Suitable polycations can be linear, such as linear tetralysine, branched or dendrimeric in structure.

Exemplary polycations include, but are not limited to, synthetic polycations based on acrylamide and 2-acrylamido-2-methylpropanetrimethylamine, poly(N-ethyl-4-vinylpyridine) or similar quarternized polypyridine, diethylaminoethyl polymers and dextran conjugates, polymyxin B sulfate, lipopolyamines, poly(allylamines) such as the strong polycation poly(dimethyldiallylammonium chloride), polyethyleneimine, polybrene, and polypeptides such as protamine, the histone polypeptides, polylysine, polyarginine and polyornithine.

In some embodiments, the polycation is a polyamine. Polyamines are compounds having two or more primary amine groups. Suitable naturally occurring polyamines include, but are not limited to, spermine, spermidine, cadaverine and putrescine. In a preferred embodiment, the polyamine is spermidine.

In another embodiment, the polycation is a cyclic polyamine. Cyclic polyamines are known in the art and are described, for example, in U.S. Pat. No. 5,698,546, WO 1993/012096 and WO 2002/010142. Exemplary cyclic polyamines include, but are not limited to, cyclen.

Spermine and spermidine are derivatives of putrescine (1,4-diaminobutane) which is produced from L-ornithine by action of ODC (ornithine decarboxylase). L-ornithine is the product of L-arginine degradation by arginase. Spermidine is a triamine structure that is produced by spermidine synthase (SpdS) which catalyzes monoalkylation of putrescine (1,4-diaminobutane) with decarboxylated S-adenosylmethionine (dcAdoMet) 3-aminopropyl donor. The formal alkylation of both amino groups of putrescine with the 3-aminopropyl donor yields the symmetrical tetraamine spermine. The biosynthesis of spermine proceeds to spermidine by the effect of spermine synthase (SpmS) in the presence of dcAdoMet. The 3-aminopropyl donor (dcAdoMet) is derived from 5-adenosylmethionine by sequential transformation of L-methionine by methionine adenosyltransferase followed by decarboxylation by AdoMetDC (S-adenosylmethionine decarboxylase). Hence, putrescine, spermidine and spermine are metabolites derived from the amino acids L-arginine (L-ornithine, putrescine) and L-methionine (dcAdoMet, aminopropyl donor).

III. Methods of Using the Particles/Micelles

A. Methods for Transfection

Transfection is carried out by contacting cells with the solution containing the polyplexes. For in vivo methods, the contacting typically occurs in vivo after the solution is administered to the subject. For in vitro methods, the solution is typically added to a culture of cells and allowed to contact the cells for minutes, hours, or days. The cells can subsequently be washed to move excess polyplexes.

The disclosed compositions can be for cell transfection of polynucleotides. As discussed in more detail below, the transfection can occur in vitro or in vivo, and can be applied in applications including gene therapy and disease treatment. The compositions can be more efficient, less toxic, or a combination thereof when compared to a control. In some embodiments, the control is cells treated with an alternative transfection reagent such as LIPOFECTAMINE 2000 or polyethylenimine (PEI).

The particular polynucleotide delivered by the polyplex can be selected by one of skill in the art depending on the condition or disease to be treated. The polynucleotide can be, for example, a gene or cDNA of interest, a functional nucleic acid such as an inhibitory RNA, a tRNA, an rRNA, or an expression vector encoding a gene or cDNA of interest, a functional nucleic acid a tRNA, or an rRNA. In some embodiments two or more polynucleotides are administered in combination.

In some embodiments, the polynucleotide encodes a protein. Exemplary proteins include, for example, (a) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor-α, hepatocyte growth factor and insulin-like growth factor; (b) cell cycle inhibitors such as cyclin-dependent kinases, thymidine kinase ("TK"), and other agents useful for interfering with cell proliferation; (c) bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. BMPs are typically dimeric proteins that can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

In some embodiments, the polynucleotide is not integrated into the host cell's genome (i.e., remains extrachromosomal). Such embodiments can be useful for transient or regulated expression of the polynucleotide, and reduce the risk of insertional mutagenesis. Therefore, in some embodiments, the polyplexes are used to deliver mRNA or non-integrating expression vectors that are expressed transiently in the host cell.

In a preferred embodiment, the polynucleotide is a pro-apoptotic construct, for example an expression vector encoding TNF-related apoptosis-inducing ligand (TRAIL), which is targeted to tumor cells.

In some embodiments, the polynucleotide is integrated into the host cell's genome. For example, gene therapy is a technique for correcting defective genes responsible for disease development. Researchers may use one of several approaches for correcting faulty genes: (a) a normal gene can be inserted into a nonspecific location within the genome to replace a nonfunctional gene. This approach is most common; (b) an abnormal gene can be swapped for a normal gene through homologous recombination; (c) an abnormal gene can be repaired through selective reverse mutation, which returns the gene to its normal function; (d) the regulation (the degree to which a gene is turned on or off) of a particular gene can be altered.

Gene therapy can include the use of viral vectors, for example, adenovirus, adeno-associated virus, herpes virus, vaccinia virus, polio virus, AIDS virus, neuronal trophic virus, Sindbis and other RNA viruses, including these viruses with the HIV backbone. Also useful are any viral families which share the properties of these viruses which make them suitable for use as vectors. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA.

Gene targeting via target recombination, such as homologous recombination (HR), is another strategy for gene correction. Gene correction at a target locus can be mediated by donor DNA fragments homologous to the target gene (Hu, et al., Mol. Biotech., 29:197-210 (2005); Olsen, et al., J. Gene Med., 7:1534-1544 (2005)). One method of targeted recombination includes the use of triplex-forming oligonucleotides (TFOs) which bind as third strands to homopurine/homopyrimidine sites in duplex DNA in a sequence-specific manner. Triplex forming oligonucleotides can interact with either double-stranded or single-stranded nucleic acids.

Methods for targeted gene therapy using triplex-forming oligonucleotides (TFO's) and peptide nucleic acids (PNAs) are described in U.S. Published Application No. 20070219122 and their use for treating infectious diseases such as HIV are described in U.S. Published Application No. 2008050920. The triplex-forming molecules can also be tail clamp peptide nucleic acids (tcPNAs), such as those described in U.S. Published Application No. 2011/0262406. Highly stable PNA:DNA:PNA triplex structures can be formed from strand invasion of a duplex DNA with two PNA strands. In this complex, the PNA/DNA/PNA triple helix portion and the PNA/DNA duplex portion both produce displacement of the pyrimidine-rich triple helix, creating an altered structure that has been shown to strongly provoke the nucleotide excision repair pathway and to activate the site for recombination with the donor oligonucleotide. Two PNA strands can also be linked together to form a bis-PNA molecule.

The triplex-forming molecules are useful to induce site-specific homologous recombination in mammalian cells when used in combination with one or more donor oligonucleotides which provides the corrected sequence. Donor oligonucleotides can be tethered to triplex-forming molecules or can be separate from the triplex-forming molecules. The donor oligonucleotides can contain at least one nucleotide mutation, insertion or deletion relative to the target duplex DNA.

Double duplex-forming molecules, such as a pair of pseudocomplementary oligonucleotides, can also induce recombination with a donor oligonucleotide at a chromosomal site. Use of pseudocomplementary oligonucleotides in targeted gene therapy is described in U.S. Published Application No. 2011/0262406. Pseudocomplementary oligonucleotides are complementary oligonucleotides that contain one or more modifications such that they do not recognize or hybridize to each other, for example due to steric hindrance, but each can recognize and hybridize to complementary nucleic acid strands at the target site. In some embodiments, pseudocomplementary oligonucleotides are pseudocomplemenary peptide nucleic acids (pcPNAs). Pseudocomplementary oligonucleotides can be more efficient and provide increased target site flexibility over methods of induced recombination such as triple-helix oligonucleotides and bis-peptide nucleic acids which require a polypurine sequence in the target double-stranded DNA.

B. In Vitro Methods

The disclosed compositions can be used in a method of delivering polynucleotides to cells in vitro. For example, the polyplexes can be used for in vitro transfection of cells. The method typically involves contacting the cells with polyplex including a polynucleotide in an effective amount to introduce the polynucleotide into the cell's cytoplasm. In some embodiments, the polynucleotide is delivered to the cell in an effective amount to change the genotype or a phenotype of the cell. The cells can primary cells isolated from a subject, or cells of an established cell line. The cells can be of a homogenous cell type, or can be a heterogeneous mixture of different cells types. For example, the polyplexes can be introduced into the cytoplasm of cells from a heterogenous cell line possessing cells of different types, such as in a feeder cell culture, or a mixed culture in various states of differentiation. The cells can be a transformed cell line that can be maintained indefinitely in cell culture. Exemplary cell lines are those available from American Type Culture Collection including tumor cell lines.

Any eukaryotic cell can be transfected to produce cells that express a specific nucleic acid, for example a metabolic gene, including primary cells as well as established cell lines. Suitable types of cells include but are not limited to undifferentiated or partially differentiated cells including stem cells, totipotent cells, pluripotent cells, embryonic stem cells, inner mass cells, adult stem cells, bone marrow cells, cells from umbilical cord blood, and cells derived from ectoderm, mesoderm, or endoderm. Suitable differentiated cells include somatic cells, neuronal cells, skeletal muscle, smooth muscle, pancreatic cells, liver cells, and cardiac cells. In another embodiment, siRNA, antisense polynucleotides (including siRNA or antisense polynucleotides) or inhibitory RNA can be transfected into a cell using the compositions described herein.

The methods are particularly useful in the field of personalized therapy, for example, to repair a defective gene, de-differentiate cells, or reprogram cells. For example, target cells are first isolated from a donor using methods known in the art, contacted with the polyplexes including a polynucleotide causing a change to the in vitro (ex vivo), and administered to a patient in need thereof. Sources or cells include cells harvested directly from the patient or an allographic donor. In preferred embodiments, the target cells to be administered to a subject will be autologous, e.g. derived from the subject, or syngenic. Allogeneic cells can also be isolated from antigenically matched, genetically unrelated donors (identified through a national registry), or by using target cells obtained or derived from a genetically related sibling or parent.

Cells can be selected by positive and/or negative selection techniques. For example, antibodies binding a particular cell surface protein may be conjugated to magnetic beads and immunogenic procedures utilized to recover the desired cell type. It may be desirable to enrich the target cells prior to transient transfection. As used herein in the context of compositions enriched for a particular target cell, "enriched" indicates a proportion of a desirable element (e.g. the target cell) which is higher than that found in the natural source of the cells. A composition of cells may be enriched over a natural source of the cells by at least one order of magnitude, preferably two or three orders, and more preferably 10, 100, 200, or 1000 orders of magnitude. Once target cells have been isolated, they may be propagated by growing in suitable medium according to established methods known in the art. Established cell lines may also be useful in for the methods. The cells can be stored frozen before transfection, if necessary.

Next the cells are contacted with the disclosed composition in vitro to repair, de-differentiate, re-differentiate, and/or re-program the cell. The cells can be monitored, and the desired cell type can be selected for therapeutic administration.

Following repair, de-differentiation, and/or re-differentiation and/or reprogramming, the cells are administered to a patient in need thereof. In the most preferred embodiments, the cells are isolated from and administered back to the same patient. In alternative embodiments, the cells are isolated from one patient, and administered to a second patient. The method can also be used to produce frozen stocks of altered cells which can be stored long-term, for later use. In one embodiment, fibroblasts, keratinocytes or hematopoietic stem cells are isolated from a patient and repaired, de-differentiated, or reprogrammed in vitro to provide therapeutic cells for the patient.

C. Systemic or Local Administration

The disclosed compositions can be used in a method of delivering polynucleotides to cells in vivo. Accordingly, in some embodiments, the cell specific polyplexes including a therapeutic polynucleotide are administered systemically in vivo to a treat a disease, for example cancer.

The particles described herein can be used to deliver an effective amount of one or more therapeutic, diagnostic, and/or prophylactic agents to a patient in need of such treatment. The amount of agent to be administered can be readily determine by the prescribing physician and is dependent on the age and weight of the patient and the disease or disorder to be treated.

In some in vivo approaches, the compositions are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

D. Co-Administration

Polyplexes disclosed herein can optionally be co-administered with one or more additional active agents. Co-administration can include the simultaneous and/or sequential administration of the one or more additional active agents and the polyplexes. The one or more additional active agents and the polyplexes can be included in the same or different pharmaceutical formulation. The one or more additional active agents and the polyplexes can achieve the same or different clinical benefit. An appropriate time course for sequential administration may be chosen by the physician, according to such factors as the nature of a patient's illness, and the patient's condition. In certain embodiments, sequential administration includes the co-administration of one or more additional active agents and the nanoparticle gene carriers within a period of one week, 72 hours, 48 hours, 24 hours, or 12 hours.

The additional active agent can be chosen by the user based on the condition or disease to be treated. Example of additional active agents include, but are not limited to, vitamin supplements, nutritional supplements, anti-anxiety medication, anti-depression medication, anti-coagulants, clotting factors, anti-inflammatories, steroids such as corticosteroids, analgesic, etc.

If the disease to be treated is cancer, the polyplexes can be administered to a subject in combination with a chemotherapeutic regime, a radiological treatment, a surgical intervention, or combinations thereof. For example, in some methods, the polyplexes are co-administered with a chemotherapeutic drug or immunostimulatory drug. The disclosed compositions can be administered with an antibody or antigen binding fragment thereof specific for a growth factor receptors or tumor specific antigens. Representative growth factors receptors include, but are not limited to, epidermal growth factor receptor (EGFR; HER1); c-erbB2 (HER2); c-erbB3 (HER3); c-erbB4 (HER4); insulin receptor; insulin-like growth factor receptor 1 (IGF-1R); insulin-like growth factor receptor 2/Mannose-6-phosphate receptor (IGF-II RIM-6-P receptor); insulin receptor related kinase (IRRK); platelet-derived growth factor receptor (PDGFR); colony-stimulating factor-1 receptor (CSF-1R) (c-Fms); steel receptor (c-Kit); Flk2/Flt3; fibroblast growth factor receptor 1 (Flg/Cek1); fibroblast growth factor receptor 2 (Bek/Cek3/K-Sam); Fibroblast growth factor receptor 3; Fibroblast growth factor eceptor 4; nerve growth factor receptor (NGFR) (TrkA); BDNF receptor (TrkB); NT-3-receptor (TrkC); vascular endothelial growth factor receptor 1 (Flt1); vascular endothelial growth factor receptor 2/Flk1/KDR; hepatocyte growth factor receptor (HGF-R/Met); Eph; Eck; Eek; Cek4/Mek4/HEK; Cek5; Elk/Cek6; Cek7; Sek/Cek8; Cek9; Cek10; HEK11; 9 Ror1; Ror2; Ret; Axl; RYK; DDR; and Tie.

Additional therapeutic agents include conventional cancer therapeutics such as chemotherapeutic agents, cytokines, chemokines, and radiation therapy. The majority of chemotherapeutic drugs can be divided in to: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and the new tyrosine kinase inhibitors e.g. imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to cisplatin, carboplatin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab (HERCEPTIN®), cetuximab, and rituximab (RITUXAN® or MABTHERA®), bevacizumab (AVASTIN®), and combinations thereof.

Other agents that can be administered in combination with polyplexes include PD-1 antagonists such as an anti-B7-H1 antibody or an anti-PD-1 antibody, an anti-CTLA4 antibody, a mitosis inhibitor, such as paclitaxel, an aromatase inhibitor, such as letrozole, an A2AR antagonist, an angiogenesis inhibitor, anthracyclines, oxaliplatin, doxorubicin, TLR4 antagonists, and IL-18 antagonists.

E. Disorders and Diseases to be Treated

The polymers described herein can be used for drug delivery, for example, in the formation of particles, such as microparticles or nanoparticles, or micelles which can release one or more therapeutic, prophylactic, and/or diagnostic agents in a controlled release manner over a desirable period of time.

Various pH-responsive micelle nanocarriers have been investigated previously. Such micelles are often formed via self-assembly of amphiphilic block copolymers and consist of a hydrophilic (e.g. PEG) outer shell and a hydrophobic inner core capable of response to medium pH. Typically, upon changing the medium pH from neutral or slightly basic to mildly acidic, the micelle cores undergo accelerated degradation, become completely soluble in water, or swell substantially in aqueous medium. As the result, the drug-encapsulated micelles with a slow drug-release rate at the physiological pH can be triggered by an acidic pH to rapidly unload the drug molecules. The polymer segments constituting the micelle cores in previous reports include poly (ortho esters), poly(β-amino esters), poly(L-histidine), and others. The major disadvantages with most of the previous micelle systems are the multiple steps required for preparing the copolymers and the difficulty of controlling the polymer molecular weight and adjusting the polymer composition during the copolymer synthesis.

It is known that upon uptake of micelles by tumor cells, the micelle particles are subjected to entrapment in endosomes with pH ranging from 5.5 to 6.0 and in lysosomes with pH ranging from 4.5 to 5.0. The amino groups in the copolymers would act as proton sponges to facilitate endosomal escape. Therefore, the pH-responsive properties of copolymer micelles are highly desirable, which render them to be superior carriers for delivery of anticancer drugs.

The compositions and methods applicable for gene therapy protocols and the treatment of gene related diseases or disorders. Cell dysfunction can also be treated or reduced using the disclosed compositions and methods. In some embodiments, diseases amenable to gene therapy are specifically targeted. The disease can be in children, for example individuals less than 18 years of age, typically less than 12 years of age, or adults, for example individuals 18 years of age or more. Thus, embodiments of the present disclosure are directed to treating a host diagnosed with a disease, by transfection of the polyplex including a polynucleotide into the cell affected by the disease and wherein the polynucleotide encodes a therapeutic protein. In another embodiment, an inhibitory RNA is directed to a specific cell type or state to reduce or eliminate the expression of a protein, thereby achieving a therapeutic effect. The present disclosure encompasses manipulating, augmenting or replacing genes to treat diseases caused by genetic defects or abnormalities.

Suitable genetic based diseases that can be treated with the compositions disclosed herein include but are not limited to:

Mitochondrial Disease:

Alpers Disease; Barth syndrome; β-oxidation defects; carnitine-acyl-carnitine deficiency; carnitine deficiency; co-enzyme Q10 deficiency; Complex I deficiency; Complex II deficiency; Complex III deficiency; Complex IV deficiency; Complex V deficiency; cytochrome oxidase (COX) deficiency, LHON—Leber Hereditary Optic Neuropathy; MM—Mitochondrial Myopathy; LIMM—Lethal Infantile Mitochondrial Myopathy; MMC—Maternal Myopathy and Cardiomyopathy; NARP—Neurogenic muscle weakness, Ataxia, and Retinitis Pigmentosa; Leigh Disease; FICP—Fatal Infantile Cardiomyopathy Plus, a MELAS-associated cardiomyopathy; MELAS—Mitochondrial Encephalomyopathy with Lactic Acidosis and Strokelike episodes; LDYT—Leber's hereditary optic neuropathy and Dystonia; MERRF—Myoclonic Epilepsy and Ragged Red Muscle Fibers; MHCM—Maternally inherited Hypertrophic CardioMyopathy; CPEO—Chronic Progressive External Ophthalmoplegia; KSS—Kearns Sayre Syndrome; DM—Diabetes Mellitus; DMDF Diabetes Mellitus+DeaFness; CIPO—Chronic Intestinal Pseudoobstruction with myopathy and Ophthalmoplegia; DEAF—Maternally inherited DEAFness or aminoglycoside-induced DEAFness; PEM—Progressive encephalopathy; SNHL—SensoriNeural Hearing Loss; Encephalomyopathy; Mitochondrial cytopathy; Dilated Cardiomyopathy; GER—Gastrointestinal Reflux; DEMCHO—Dementia and Chorea; AMDF—Ataxia, Myoclonus; Exercise Intolerance; ESOC Epilepsy, Strokes, Optic atrophy, & Cognitive decline; FBSN Familial Bilateral Striatal Necrosis; FSGS Focal Segmental Glomerulosclerosis; LIMM Lethal Infantile Mitochondrial Myopathy; MDM Myopathy and Diabetes Mellitus; ME PR Myoclonic Epilepsy and Psychomotor Regression; MERME MERRF/MELAS overlap disease; MHCM Maternally Inherited Hypertrophic CardioMyopathy; MICM Maternally Inherited Cardiomyopathy; MILS Maternally Inherited Leigh Syndrome; Mitochondrial Encephalocardiomyopathy; Multisystem Mitochondrial Disorder (myopathy, encephalopathy, blindness, hearing loss, peripheral neuropathy); NAION Nonarteritic Anterior Ischemic Optic Neuropathy; NIDDM Non-Insulin Dependent Diabetes Mellitus; PEM Progressive Encephalopathy; PME Progressive Myoclonus Epilepsy; RTT Rett Syndrome; SIDS Sudden Infant Death Syndrome; MIDD Maternally Inherited Diabetes and Deafness; and MODY Maturity-Onset Diabetes of the Young.

Nuclear Disease:

Muscular Dystrophies, Ellis-van Creveld syndrome, Marfan syndrome, Myotonic dystrophy, Spinal muscular atrophy, Achondroplasia, Amyotrophic lateral sclerosis, Charcot-Marie-Tooth syndrome, Cockayne syndrome, Diastrophic dysplasia, Duchenne muscular dystrophy, Ellis-van Creveld syndrome, Fibrodysplasia ossificans progressive, Alzheimer disease, Angelman syndrome, Epilepsy, Essential tremor, Fragile X syndrome, Friedreich's ataxia, Huntington disease, Niemann-Pick disease, Parkinson disease, Prader-Willi syndrome, Rett syndrome, Spinocerebellar atrophy, Williams syndrome, Ataxia telangiectasia, Anemia, sickle cell, Burkitt lymphoma, Gaucher disease, Hemophilia, Leukemia, Paroxysmal nocturnal hemoglobinuria, Porphyria, Thalassemia, Crohn's disease, Alpha-1-antitrypsin deficiency, Cystic fibrosis, Deafness, Pendred syndrome, Glaucoma, Gyrate atrophy of the choroid and retina, Adrenal hyperplasia, Adrenoleukodystrophy, Cockayne syndrome, Long QT syndrome, Immunodeficiency with hyper-IgM, Alport syndrome, Ellis-van Creveld syndrome, Fibrodysplasia ossificans progressive, Waardenburg syndrome, Werner syndrome.

Infectious Disease:

Viral—AIDS, AIDS Related Complex, Chickenpox (Varicella), Common cold, Cytomegalovirus Infection, Colorado tick fever, Dengue fever, Ebola haemorrhagic fever, Epidemic parotitis, Flu, Hand, foot and mouth disease, Hepatitis—Herpes simplex, Herpes zoster, HPV, Influenza, Lassa fever, Measles, Marburg haemorrhagic fever, Infectious mononucleosis, Mumps, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease—Yellow fever; Bacterial—Anthrax, Bacterial Meningitis, Brucellosis, Bubonic plague, Campylobacteriosis, Cat Scratch Disease, Cholera, Diphtheria, Epidemic Typhus, Gonorrhea, Hansen's Disease, Legionellosis, Leprosy, Leptospirosis, Listeriosis, Lyme Disease, Melioidosis, MRSA infection, Nocardiosis, Pertussis, Pneumococcal pneumonia, Psittacosis, Q fever, Rocky Mountain Spotted Fever or RMSF, Salmonellosis, Scarlet Fever, Shigellosis, Syphilis, Tetanus, Trachoma, Tuberculosis, Tularemia, Typhoid Fever, Typhus, Whooping Cough; Parasitic—African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, Trypanosomiasis.

Cancers:

Breast and ovarian cancer, Burkitt lymphoma, Chronic myeloid leukemia, Colon cancer, Lung cancer, Malignant melanoma, Multiple endocrine neoplasia, Neurofibromatosis, p53 LieFrauMeni, Pancreatic cancer, Prostate cancer, retinoblastoma, von Hippel-Lindau syndrome, Polycystic kidney disease, Tuberous sclerosis.

Metabolic Disorders:

Adrenoleukodystrophy, Atherosclerosis, Best disease, Gaucher disease, Glucose galactose malabsorption, Gyrate atrophy, Juvenile onset diabetes, Obesity, Paroxysmal nocturnal hemoglobinuria, Phenylketonuria, Refsum disease, Tangier disease, Tay-Sachs disease, Adrenoleukodystrophy, Type 2 Diabetes, Gaucher disease, Hereditary hemochromatosis, Lesch-Nyhan syndrome, Maple syrup urine disease, Menkes syndrome, Niemann-Pick disease, Pancreatic cancer, Prader-Willi syndrome, Porphyria, Refsum disease, Tangier disease, Wilson's disease, Zellweger syndrome, progerias, SCID.

Autoimmune Disorders:

Autoimmune polyglandular syndrome, lupus, type I diabetes, scleroderma, multiple sclerosis, Crohn's disease, chronic active hepatitis, rheumatoid arthritis, Graves' disease, myasthenia gravis, myositis, antiphospholipid syndrome (APS), uveitis, polymyositis, Raynaud's phenomenon, and demyelinating neuropathies, and rare disorders such as polymyalgia rheumatica, temporal arteritis, Sjogren's syndrome, Bechet's disease, Churg-Strauss syndrome, and Takayasu's arteritis.

Inflammatory Disorders:

Alopecia, Diastrophic dysplasia, Ellis-van Creveld syndrome, Asthma, Arthritis, including osteoarthritis, rheumatoid arthritis, and spondyloarthropathies.

Age-Related Disorders:

Alzheimer Disease, Parkinson's Disease, Atherosclerosis, Age-Related Macular Degeneration, Age-related Osteoporosis.

The disclosed methods and compositions can also be used to treat, manage, or reduce symptoms associated with aging, in tissue regeneration/regenerative medicine, stem cell transplantation, inducing reversible genetic modifications, expressing inhibitory RNA, cognitive enhancement, performance enhancement, and cosmetic alterations to human or non-human animal.

F. Research Tools

In one embodiment, the present disclosure is used as a tool to investigate cellular consequences of gene expression. Mutant mice can be generated using this approach, allowing investigators to study various biological processes. More particularly, the methods and compositions disclosed herein can be used to generate cells that contain unique gene modifications known in the art and at the discretion of one skilled in the art.

G. Transgenic Non-Human Animals

The techniques described herein can also be used to generate transgenic non-human animals, since they have the potential to efficiently deliver genetic materials, including DNA, siRNA, triplex forming oligonucleotides or CRISPR/Cas9, to a variety of cells, including embryonic stem (ES) cells and germ cells. In particular, zygote microinjection, nuclear transfer, blastomere electrofusion and blastocyst injection of embryonic stem (ES) cell cybrids have each provided feasible strategies for creating transgenic animals. In one embodiment an embryonic stem (ES) cell is transfected and injected into the blastocyst of a mammalian embryo as a means of generating chimeric mice. In another embodiment, embryonic stem (ES) cell are first prepared, followed by blastocyst injection into embryos. The use of cells carrying specific genes and modifications of interest allows the creation and study of the consequences of the transfected DNA. In theory, this technique offers the prospect of transferring any polynucleotide into a whole organism. For example, the disclosed methods and compositions could be used to create mice possessing the delivered polynucleotide in a specific cell type or cell state.

Another embodiment of the disclosure provides transfected non-human organisms and methods making and using them. Single or multicellular non-human organisms, preferably non-human mammals, more preferably mice, can be transfected with the compositions described herein by administering the compositions of the present disclosure to the non-human organism. In one embodiment, the polynucleotide remains episomal and does not stably integrate into the genome of the host organism. In another embodiment, the polynucleotide prevents the expression of a gene of interest. Thus, the expression of the polynucleotide in specific cells of the host can be controlled by the amount of polynucleotide administered to the host.

H. Kits

Kits or packs that supply the elements necessary to conduct transfection of eukaryotic or prokaryotic organisms, in particular the transfection of specific cell types or cell states are also disclosed. In accordance with one embodiment a kit is provided comprising the disclosed polymers, and optionally a polyplex coating, for example a target specific coating. The polymer can be combined with a polynucleotide of the user's choosing to form a complex which can be used to transfect a host or a host cell. The polyplex can be further mixed with the coating to provide cell-type or cell-state specific tropism.

The individual components of the kits can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

EXAMPLES

Example 1: Synthesis and Characterization of Poly(Amine-co-Ester-co-Ortho Ester) Quaterpolymers Materials and Methods
Materials ω-pentadecalactone (PDL), diethyl sebacate (DES), N-methyldiethanolamine (MEDA), 3,9-Divinyl-2,4,8,10-tetraoxaspiro[5.5]undecane (DTSU), ethyl glycolate, ethyl 6-hydroxy hexanoate and methyl 10-hydroxydecanoate were purchased from Aldrich Chemical Co. and were used as received. Immobilized *Candida antarctica* lipase B (CALB) supported on acrylic resin (Novozym 435), potassium t-butoxide, chloroform, dichloromethane, hexane, pentane, diphenyl ether, tetrahydrofuran, ethylene diamine, triethylamine and chloroform-d were also obtained from Aldrich Chemical Co. The lipase catalyst was dried at 50° C. under 2.0 mmHg for 20 h prior to use.

HEK293 cells and U87MG cells were obtained from American Type Culture Collection (Manassas, Va.) and grown at 37° C. under 5% $CO_2$ atmosphere in Dulbecco's modified Eagle's medium (DMEM) containing 10% fetal bovine serum and 1% penicillin-streptomycin. Plasmid DNA (pGL4.13) encoding the firefly luciferase (pLucDNA) and Luciferase Assay Buffer were obtained from Promega Co. (Madison, Wis.). GFP reporter gene pSicoR-GFP (pGFP) was obtained from Addgene.

Instrumentation Methods $^1H$ and $^{13}C$ NMR spectra were recorded on a Bruker AVANCE 500 spectrometer. The chemical shifts reported were referenced to internal tetramethylsilane (0.00 ppm) or to the solvent resonance at the appropriate frequency. The number and weight average molecular weights (Mn and Mw, respectively) of polymers were measured by gel permeation chromatography (GPC) using a Waters HPLC system equipped with a model 1515 isocratic pump, a 717 plus autosampler, and a 2414 refractive index (RI) detector. Empower II GPC software was used for running the GPC instrument and for calculations. Columns and the RI detector were heated and maintained at 40° C. temperature during sample analysis. Chloroform was used as the eluent at a flow rate of 1.0 mL/min. Sample concentrations of 2 mg/mL and injection volumes of 100 μL were used. Polymer molecular weights were determined based on a conventional calibration curve generated by narrow polydispersity polystyrene standards from Aldrich Chemical Co. The morphology of polyplexes, which was stained with uranyl acetate, was visualized using a Zeiss EM 900 transmission electron microscope (TEM).

Synthesis of Ortho Ester Diester Monomers

DTSU was isomerized in ethylene diamine with potassium t-butoxide as catalyst, to produce 3,9-diethylidene-2,4,8,10-tetraoxaspiro[5.5]undecane (DETOSU)[1]. Following the synthesis of DETOSU, 2 mole of ethyl glycolate (n=1), ethyl 6-hydroxyhexanoate (n=5), or methyl 10-hydroxydecanoate (n=9) was added to 1 mole of DETOSU and the reaction was carried out at room temperature in THF catalyzed by p-toluenesulfonic acid. Three different ortho ester diesters (OEDEs) were obtained with quantitative yield, which are designated as OEDE(1), OEDE(5) and OEDE(9), respectively. All the structures were confirmed by $^1H$ and $^{13}C$ NMR.

Synthesis and Purification of Poly(Amine-co-Ester-co-Ortho Ester

The copolymerization of PDL, diethyl sebacate (DES), MEDA and OEDE(n=1, 5, 9) was performed in diphenyl ether solution using a parallel synthesizer connected to a vacuum line with the vacuum (±0.2 mmHg) controlled by a digital vacuum regulator. In a typical experiment, reaction mixtures were prepared, which contained all four monomers, Novozym 435 catalyst (10 wt % versus total monomer), and diphenyl ether solvent (200 wt % versus total monomer). The copolymerization reactions were carried out at 90° C. in two stages: first-stage oligomerization, followed by second-stage polymerization. During the first-stage reaction, the reaction mixtures were stirred under 1 atm of nitrogen gas, after which the reaction pressure was reduced to 1.6 mmHg and the reactions were continued for a further 72 h. The quaterpolymer products were isolated and purified by precipitation in hexane first, and then washed several times with fresh hexane to extract and remove the residual diphenyl ether solvent from the polymers. Subsequently, the quaterpolymers were dissolved in dichloromethane and filtered to remove catalyst particles. Evaporation and complete removal of the $CH_2Cl_2$ solvent from the filtrates at 40° C. under high vacuum (1.0 mmHg) yielded the purified quaterpolymers. The structures of the polymers were confirmed by $^1H$ and $^{13}C$ NMR spectroscopy and the molecular weights were measured by GPC.

Measurement of Size, Gene Binding and Release of the Polymer/Gene Polyplex

The size of the polyplex was measured with dynamic laser scattering on a Malvern Zetasizer. For agarose gel retardation assays, DNA/polymer polyplex were prepared at different polymer:DNA weight ratio with method described previously. After the preparation, free DNA, DNA ladder and polyplexes were loaded with 15% Ficoll 400 on a 1% agarose gel and was run in sodium acetate buffer at 55V for 1 hour. DNA bands were visualized by ethidium bromide staining. For gene release study, polyplex containing 1 ug of pGL4.13 was incubated in 1 mL of 150 mM pH5 sodium acetate buffer containing 5 mM EDTA at 37° C. for 4 hours. Then, fresh polyplexes and those after incubation were incubated with different concentration of heparin at 37° C. for 15 mins. The amount of gene released was tested with Quant-it PicoGreen dsDNA assay kit (Invitrogen) and normalized to the reading from 1 ug of free DNA in same buffer.

Polymer Degradation Study

Certain amount of poly(amine-co-ester-co-ortho ester) (PACEO) and the control polymer, poly(amine-co-ester) terpolymer (PACE) were added to the bottom of glass vials, and incubated with 150 mM sodium acetate buffer of pH4, pH5, pH6 and PBS buffer at 37° C. At certain time intervals, the buffer was removed carefully and the weight of the residual polymer after drying will be measured.

In Vitro Transfection

For in vitro transfection, DNA polyplexes with polymer: DNA weight ratio of 100:1 were used unless otherwise noted. Polymers were dissolved in DMSO at 25 mg/mL. Cells were seeded in 24-well plates at density of 75,000 cells/well in 500 μL of medium one night before transfection. To preparing DNA polyplexes for transfection, 4 μL of polymer solution (25 mg/mL in DMSO) was first diluted in 50 μL sodium acetate buffer (25 mM, pH=5.2). After brief vortexing, the polymer solution was mixed with the same volume of a DNA solution containing 1 μg DNA and vortexed for additional 10 seconds. The polymer/DNA mixture was incubated at room temperature for 10 min and then added to cells. Transfection using Lipofectamine 2000 (Invitrogen Corp.) was performed using the procedures provided by the manufacturer. The same amount of DNA was used for transfection with PACEO and Lipofectamine 2000.

For luciferase gene transfection, plasmid DNA expression luciferase, pGL4.13 (Promega) was used. Two days after transfection, the culture medium was removed and the cells were washed with cold PBS. Two hundred micro-liter Report Lysis Buffer (Promega) was added to each well. After a freeze-thaw cycle, cell lysate was collected. After a quick spin, 204 was mixed with Luciferase Assay Reagent according to the standard protocol described in manufacturer manual (Promega). Total protein level was quantified using Pierce BCA protein assay kit (Pierce, Thermo Scientific). Luciferase expression was normalized to the total amount of protein in the cell lysate.

For GFP gene transfection, pSicoR-GFP was used to prepare polyplex. After 48 h of incubation, the transfected cells in each well were washed twice with PBS. Subsequently, 100 uL of trypsin was added to each well, followed by incubation at 37° C. for 3 min. The cells were then washed with PBS, suspended in 300 uL FACs buffer, and finally analyzed by BD FACS Calibur Flow Cytometer (Becton Dickinson, San Jose, Calif.).

For siRNA knockdown study, HEK293 cells stably transfected with pGL4.13 plasmid with luciferase gene were seeded in 24-well plates at density of 75,000 cells/well in 500 µl of medium one night before transfection. siRNA (5'-GCUAUGAAGCGCUAUGGGC-3') was used to knockdown the expression of luciferase. siRNA/polymer polyplexs were prepared with similar method for the preparation of pDNA/polymer polyplex. Transfection using Lipofectamine RNAiMax (Invitrogen Corp.) was performed using the procedures provided by the manufacturer. The same amount of DNA was used in transfection with polymer or Lipofectamine RNAiMAx. Two days after transfection, the luciferase expression level was measured with similar method for luciferase pDNA transfection, and was compared to control samples transfected with scrambled siRNA and no-treatment group.

In Vitro Toxicity Test

The cytotoxicity of PACEO(5)-20 and PEI was studied against HEK293 cells. The cells were seeded in 96-well plates one night before at an initial seeding density of $1.5\times10^4$ cells per well in 100 uL of DMEM. The solution of PACEO(5)-20 in DMSO was diluted in sodium acetate buffer to prepare PACEO samples of different concentration. PEI was also dissolved in sodium acetate buffer at different concentration. The concentration of DMSO in all PACEO and PEI solution was adjusted so that all samples have the same concentration of DMSO. Then, the growth medium was removed and replaced with fresh DMEM, followed by addition of 20 uL of either PACEO or PEI solution at different concentrations to each well. For control experiments, 20 uL sodium acetate buffer with the same amount of DMSO was added. After 48-h incubation, the cells were assayed for metabolic activity using a standard MTT assay.

Results

Synthesis and Purification of Poly(Amine-co-Ester-co-Ortho Ester) (PACEO)

Polyplexes formed between nucleotides and biodegradable PACEO polymers can be used for gene transfection. A family of ortho esters has been synthesized and incorporated into the polymers, in order to determine their effect on the gene transfection efficiencies of polyplexes formed from these polymers. By controlling the hydrophobicities and cation densities of the polymers used to form the polyplexes, new and improved polyplexes are produced with superior acid sensitivities, gene transfection efficiencies and low cytotoxicities compared to other known non-viral delivery agents.

All the structures were confirmed by $^1$H and $^{13}$C NMR. Table 1, above, shows the composition, weight and number average molecular weights, polydispersity, and other characterization data of selected OEDE-DES-MEDA-PDL quaterpolymers that were prepared and characterized as described above. The composition of each individual quaterpolymer is further denoted PACEO(a)-b indicating denotes the number of methylene groups between the ortho ester and the ester functional groups (a), and the percent content of the ortho ester present in the polymer (b). For example, PACEO (9)-13 represents an OEDE-DES-MEDA-PDL copolymer with nine methylene groups between the ortho ester and 13% OEDE content.

The weight average molecular weight ($M_w$) of the polymers ranged from 1000 to 21000 Daltons. In general, the PACEO(1) and PACEO(5) polymers had the lowest and highest $M_w$, respectively. It is noted that the PACEO(1) polymers have low $M_w$, because OEDE(1) is less compatible with the CALB. The polydispersity ($M_w/M_n$) ranged between 1.20 and 2.16. The PACEO(1) and PACEO(5) showed the lowest and highest overall $M_w/M_n$ values, respectively.

Measurement of Size, Gene Binding

Figure 2:
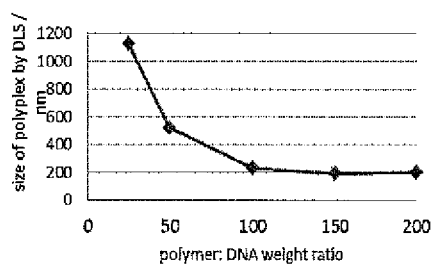
FIG. 2 shows the sizes of polyplexes formed at different polymer:DNA weight ratios. The polymer used to form the polyplex contains an ortho ester with five methylene groups between the ortho ester and the ester groups, and 20% ortho ester (PACEO(5)-20).

The size of the polyplex was measured with dynamic laser scattering on a Malvern Zetasizer, using different polymer: DNA ratios (w/w). Referring to FIG. 2, with PACEO(5)-20 as an example, the sizes of the polyplexes decreased sharply between polymer:DNA ratios of 25:1 and 100:1, from about 1200 nm to about 200 nm. The sizes of the polyplexes showed slight changes between polymer:DNA ratios of 100:1 and 200:1.

The degree of association between the polymers and DNA within the polyplexes was determined using gel retardation assays as described above. The polyplexes predominantly showed good binding between the different PACEOs and DNA, evident from the absence of free DNA across the paths of wells containing polyplexes generated with different polyper:DNA ratios. Free DNA showed significant migration across the gel. On the other hand free DNA was not observed for polyplexes formed from polymer:DNA ratios of 40:1, 60:1, 80:1, 100:1, 150:1 and 200:1. However, a small amount of free DNA was observed for the polyplex formed from a polymer:DNA ratio of 20:1. These results show that these polyplexes can carry DNA, as well as other prophylactic, diagnostic, or therapeutic agents.

Polymer Degradation Study

Figure 3A:
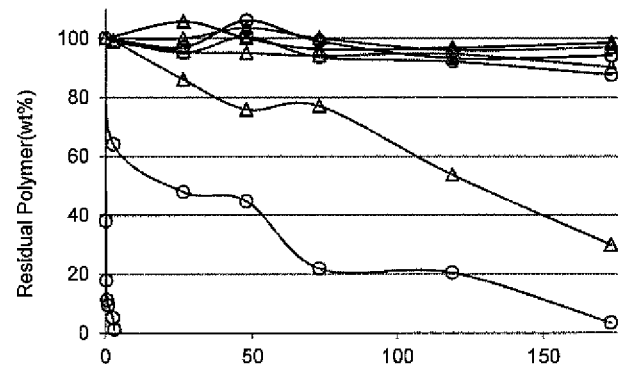
FIG. 3A shows the residual polymer (weight percent) as a function of time for the hydrolytic degradation of poly (amine-co-ester) (PACE (Δ)), and PACEO(5)-20 (O) at 37° C. in NaOAc buffer solutions 6.0 (purple), 5.0 (blue), and 4.0 (red) and PBS buffer at pH 7.4.

Polymer degradation analyses were carried out at 37° C. in sodium acetate buffer solutions at pH 7.4, 6.0, 5.0 and 4.0 using PACE as a control polymer and PACEO(5)-20, as described above. Referring to FIG. 3A, the polymers showed different stabilities with increasing acidity, shown by the differences in residual polymer weight percentages. PACE and PACEO(5)-20 were stable at the physiological pH of 7.4. At pH 6.0 both polymers were relatively stable compared to the observed stabilities at physiological pH. However, at pH 5.0 and 4.0 PACEO(5)-20 showed a drastically faster rate of degradation compared to PACE.

It is known that the compartments of endosomes, lysosomes and the extracellular matrices of septic, cancerous and necrotic tissues are more acidic compared to the systemic environment that is generally maintained at physiological pH. The acid responsive properties of PACEO in general, and PACEO(5)-20 exemplified herein, is desirable, because in systemic circulation at physiological pH the polyplexes formed from PACEO are stable and remain bound to their prophylactic, diagnostic and/or therapeutic agent(s). However, upon uptake of the PACEO polyplexes by cells, the particles are subjected to entrapment in endosomes with pH ranging from 5.5 to 6.0 and in lysosomes with pH ranging from 4.5 to 5.0. As the above results clearly show, these acidic environments would inevitably trigger fast degradation of the particles and release of prophylactic, diagnostic and/or therapeutic agent(s).

Release of the Polymer/Gene Polyplex

Figure 3B:
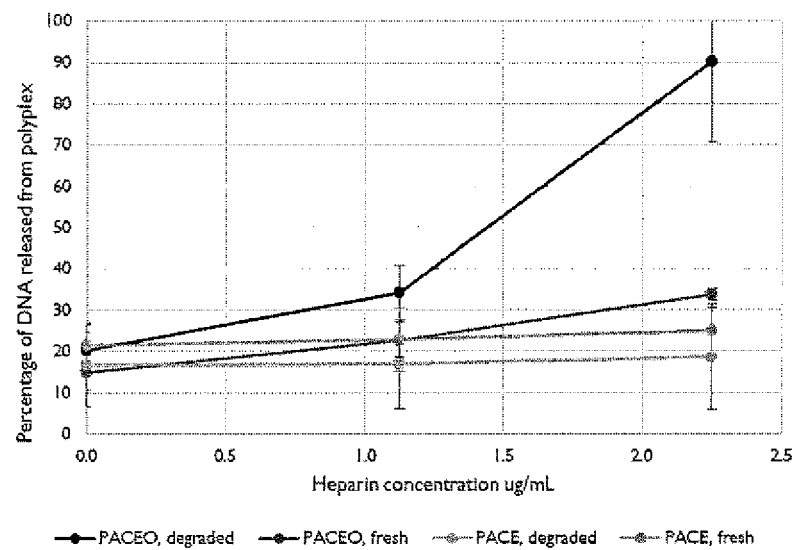
FIG. 3B shows the percentage of DNA released from fresh polyplexes or those after incubation at pH5, as a function of heparin concentration.

The release of DNA from the polyplexes was analyzed at 37° C. and pH 5.0 as a function of heparin concentration, using polyplexes formed from PACE as a control, and PACEO(9)-20. Referring to FIG. 3B, increasing the concentration of heparin remarkably increased the rate of DNA released from PACEO(9)-20 compared to PACE. Incubation at pH 5.0 weakens the binding between DNA and polymer. Heparin acts as an electrostatic competitor, further weakening the binding between the polymer-DNA complex, thereby enhancing the release of DNA.

In Vitro Transfection

Figure 4A:
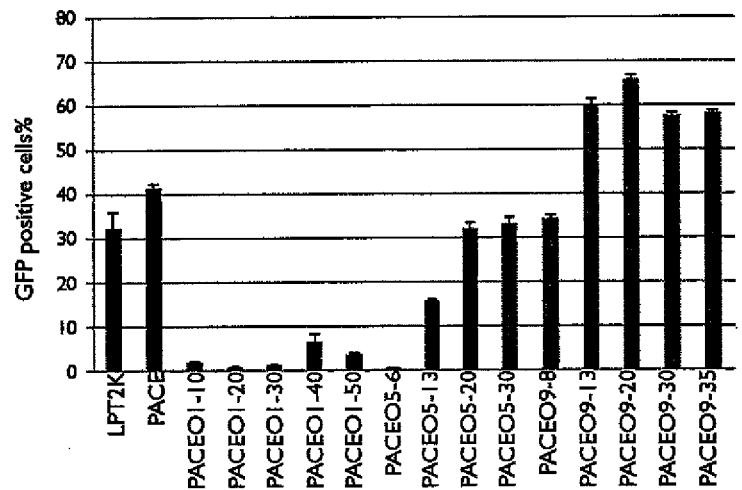
FIG. 4A shows the percent of GFP positive cells for U87 cells transfected in vitro using different polyplexes. GFP expression was measured 48 hours after transfection with GFP reporter gene, pScioR-GFP. Polymer:DNA weight ratio is 100:1, lipofectamine transfection was performed according to manufacturer's protocol. 1 μg of DNA per well of a 24-well plate is used in each sample.

To assess the gene transfection efficiencies of the polyplexes, GFP reporter gene, pSicoR-GFP was used to prepare the polyplex. U87 cells are used here, and GFP expression was measured 48 hours after transfection. Polymer:DNA weight ratio was 100:1. A series of PACEO polymers were used to form the polyplexes. Other non-viral gene delivery vectors such as PACE, and the commercially available lipofectamine 2000 were also used. Referring to FIG. 4A, the majority of the PACEO polyplexes were more efficient than the commercially available lipofectamine 2000. PACEO(9)-13, PACEO(9)-20, PACEO(9)-30, and PACEO(9)-35 were more efficient than PACE.

The percent content of the ortho ester in the polymer influenced the transfection efficiencies of the polyplexes, FIG. 4A. For example increasing the content of the ortho ester generally increased the transfection efficiencies of the PACEO(5) and PACEO(9) polyplexes. Unexpectedly, it was found that the number of methylene groups between the ortho ester and the ester groups had a big impact on transfection efficiencies. For example, the transfection efficiency of PACEO(9)-13 was about 60%, while that of PACEO(5)-13 was only about 15%. Furthermore, the transfection efficiency of PACEO(9)-20 was about 66%, while that of PACEO(5)-20 was about 32%.

Figure 4B:
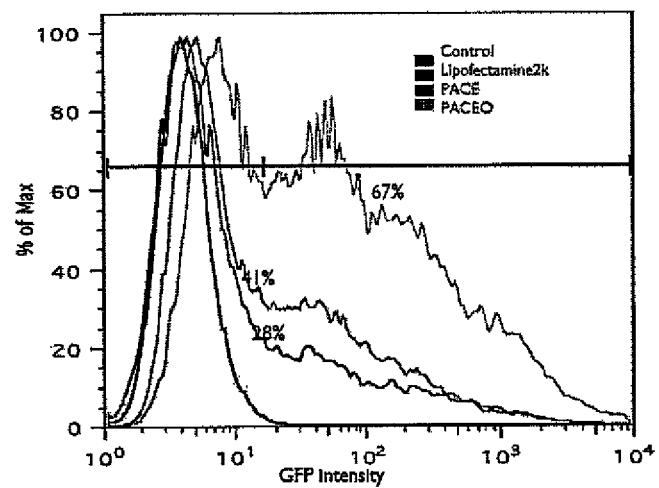
FIG. 4B is a histogram of flow cytometry analysis for GFP intensity using different polyplexes.

FIG. 4B is a histogram showing the gene transfection efficiencies of a PACEO polyplex monitored using flow cytometry. Analyses of the GFP intensity showed that PACEO was a more efficient gene delivery agent than PACE, lipofectamine 2000 and control.

Figure 5A:
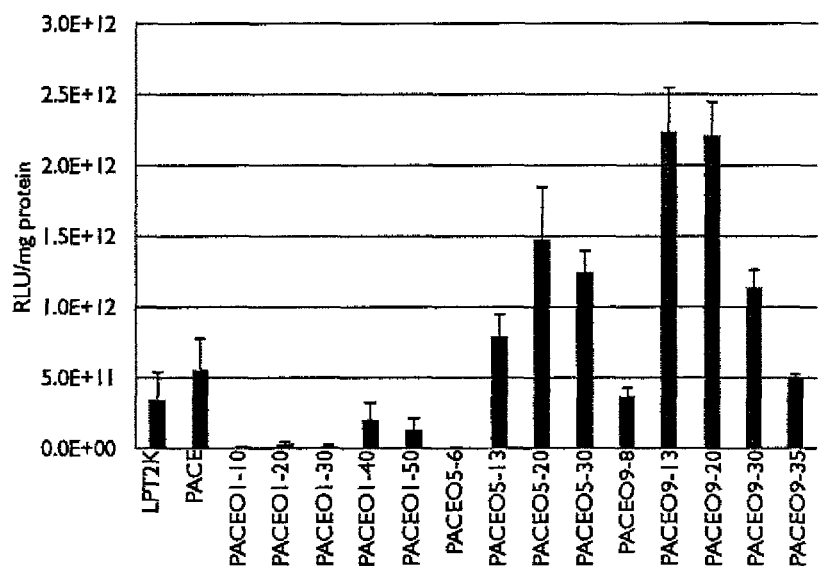
FIG. 5A shows the relative light unit (RLU)/mg of total cell protein for HEK293 cells transfected using different polyplexes. Luciferase expression was measured 48 hours after transfection with Luciferase reporter gene, pGL4.13. Polymer:DNA weight ratio is 100:1, lipofectamine transfection was performed according to manufacturer's protocol. 1 μg of DNA per each well of 24-well plate is used in each sample.
Figure 5B:
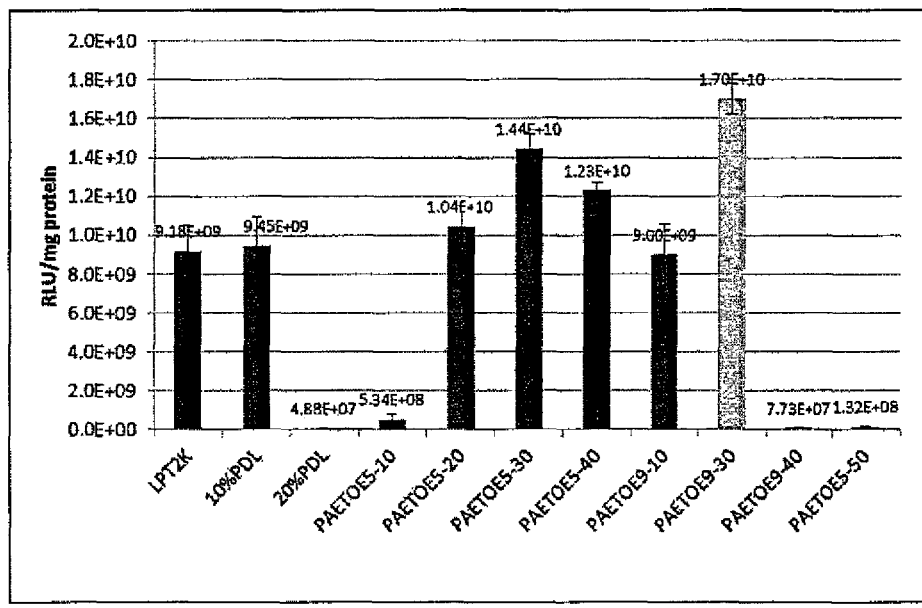
FIG. 5B shows the RLU/mg of protein a primary mouse melanoma cell line cells transfected using different polyplexes. Luciferase expression was measured 48 hours after transfection with Luciferase reporter gene, pGL4.13. Polymer:DNA weight ratio is 100:1, lipofectamine transfection was performed according to manufacturer's protocol. 1 μg of DNA per each well of 24-well plate is used in each sample.

The gene transfection efficiency (RLU/mg of protein) of polyplexes formed from several polymers, as labeled, for HEK293 are shown in FIG. 5A. Luciferase expression was measured 48 hours after transfection with Luciferase reporter gene, pGL4.13. Polymer:DNA weight ratio is 100:1, lipofectamine transfection was performed according to manufacturer's protocol. The same amount of DNA is used in each sample. The transfection efficiency was influenced by the percent content of the ortho ester. Remarkably, the number of methylene groups between the ortho ester and the ester groups significantly affected the efficiency of transfection. For example, PACEO(9)-13 and PACEO(9)-20 had 2.8-fold and 1.5-fold higher transfection efficiencies than PACEO(5)-13 and PACEO(5)-20. Additional comparisons between the transfection efficiencies (RLU/mg of protein) amongst polyplexes formed from the PACEO polymers and other polymers are shown in FIG. 5B. Luciferase expression was measured 48 hours after transfection with Luciferase reporter gene, pGL4.13. Polymer:DNA weight ratio is 100:1, lipofectamine transfection was performed according to manufacturer's protocol. 1 ug of DNA per well of a 24-well plate is used in each sample. Luciferase expression was measured 48 hours after transfection.

Figure 6:
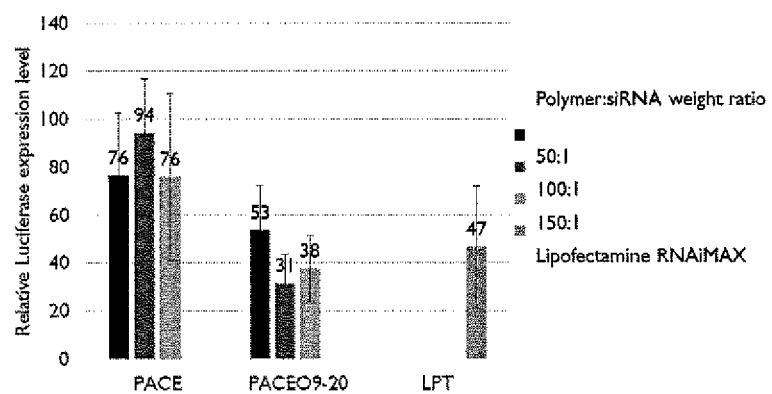
FIG. 6 shows the relative luciferase expression levels in HEK293 cells transfected with siLuc using PACE, PACEO (9)-20 and lipofectamine RNAiMax. HEK293 Cells were transfected with siLuc for 2 days by different agents.

The efficiencies of the polyplexes to silence gene express products in HEK293 cells was compared using PACE, PACEO(9)-20 and lipofectamine 2000, using different polymer:siRNA weight ratios, as described above for siRNA knockdown studies. Referring to FIG. 6, PACEO(9)-20 was more efficient at silencing the expression of luciferase compared to PACE. In addition, PACEO(9)-20 was more efficient than the commercially available lipofectamine 2000 polymer:DNA ratios (w/w) of 100:1 and 150:1.

In Vitro Toxicity Test

Figure 7:
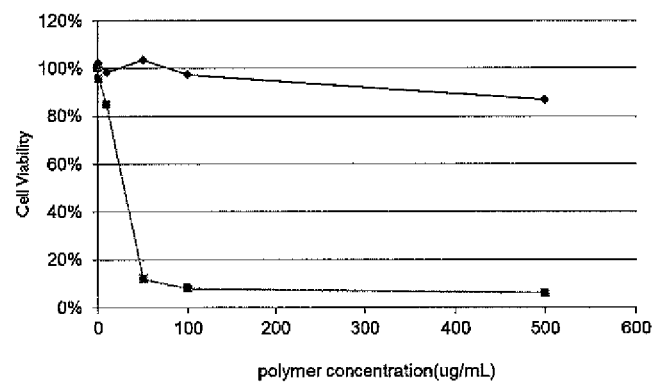
FIG. 7 shows HEK293 cell viability as a function of the concentrations of the polymers used to form PACEO(5)-20 (blue) and PEI (pink) polyplexes. HEK293 cells were treated with PACEO(5)-20 or PEI for 2 days.

The cytotoxicities of unloaded PACEO(5)-20 and PEI were evaluated as described above. Referring to FIG. 7, PACEO(5)-20 showed superior cell viability properties compared to PEI. At the highest polymer concentration assessed more than 80% of the cells were still viable with PACEO(5)-20, while less than 10% of the cells were viable with PEI.

We claim:

1. A polymeric formulation for delivery of a nucleic acid comprising a poly(amine-co-ester-co-ortho ester) or poly(amine-co-amide-co-ortho ester) having the following formula:

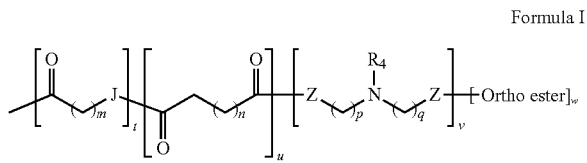

Formula I wherein each occurrence of m is an integer from 1-30,
each occurrence of n, p, and q is independently an integer from 1-20, and
each occurrence of t, u, v, and w is independently an integer from 1-1000,
J and Z are independently O or NR', wherein R' is hydrogen, substituted or unsubstituted alkyl, or substituted or unsubstituted aryl,
wherein $R_4$ is hydrogen, alkyl, substituted alkyl, alkenyl, substituted alkenyl, alkynyl, substituted alkynyl, aryl, substituted aryl, heteroaryl, substituted heteroaryl, alkoxy, substituted alkoxy, aroxy, substituted aroxy, alkylthio, substituted alkylthio, arylthio, substituted arylthio, amino, substituted amino, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group,
wherein the ortho ester has the following formula:

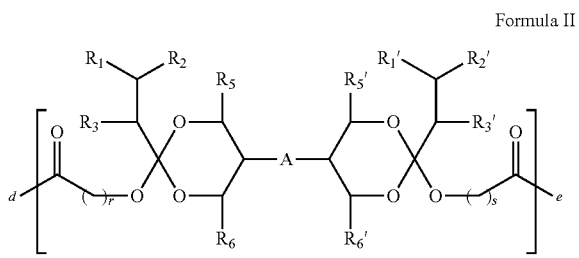

Formula II wherein r and s are independently an integer from 1-20,
wherein A is absent or A is a single bond,
wherein $R_1$, $R_1'$, $R_2$, $R_2'$, $R_3$, $R_3'$, $R_5$, $R_5'$, $R_6$ and $R_6'$ groups are independently hydrogen, alkyl, substituted alkyl, alkenyl, substituted alkenyl, alkynyl, substituted alkynyl, aryl, substituted aryl, heteroaryl, substituted heteroaryl, alkoxy, substituted alkoxy, aroxy, substituted aroxy, alkylthio, substituted alkylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group,
wherein the ortho ester is attached to the rest of the polymer at points d and/or e, and
wherein the arrangements of the units within the polymer are ordered or random.

2. The formulation of claim 1 wherein J and Z are each O.

3. The formulation of claim 1 wherein J and Z are each O, and m is an integer from 1-16.

4. The formulation of claim 1 wherein J and Z are each O, m is an integer from 1-16, and n is an integer from 1-10.

5. The formulation of claim 1 wherein J and Z are each O, m is an integer from 1-16, n is an integer from 1-10, and p and q are the same integer from 1-6.

6. The formulation of claim 1 wherein J and Z are each O, m is an integer from 1-16, n is an integer from 1-10, and $R_4$ is alkyl.

7. The formulation of claim 1 wherein J and Z are each O, m is an integer from 1-16, n is an integer from 1-10, $R_4$ is alkyl, or aryl and r and s are the same integer from 1-20.

8. The formulation of claim 1 wherein J and Z are each O, m is an integer from 1-16, n is an integer from 1-10, $R_4$ is alkyl, r and s are the same integer from 1-20, and $R_1$, $R_1'$, $R_2$, $R_2'$, $R_3$, $R_3'$, $R_5$, $R_5'$, $R_6$ and $R_6'$ are each a hydrogen atom.

9. The formulation of claim 1 wherein m is 14, n is 7, p and q are 2, and $R_4$ is methyl, r and s are 1, 5, or 9.

10. The formulation of claim 1 wherein the arrangements of the units within the polymer are random.

11. The formulation of claim 1 further comprising an alkylene oxide, selected from the group consisting of polyethylene oxide, polypropylene oxide, and/or polyethylene oxide-co-polypropylene oxide.

12. The formulation of claim 11 having the formula:

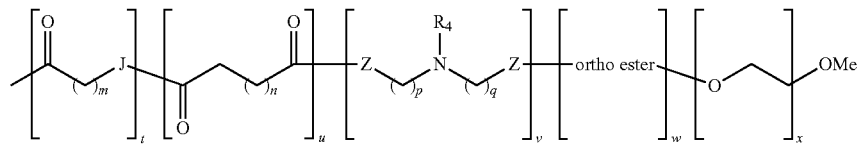

wherein m is an integer from 1-30,
n, p, and q are independently an integer from 1-20,
t, u, v, w and x are independently integers from 1-1000, and
J and Z are independently 0 or NR', wherein R' is hydrogen, substituted or unsubstituted alkyl, or substituted or unsubstituted aryl.

13. The formulation of claim 12 wherein the arrangements of the units within the polymer are random.

14. The formulation of claim 11, wherein the polymer has the structure:

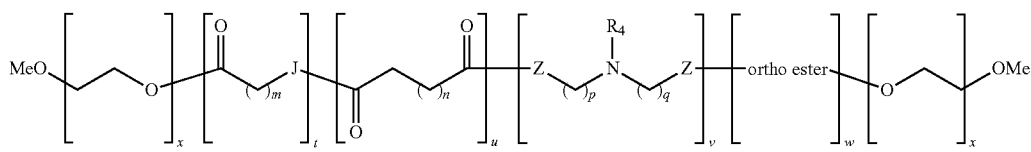

wherein m is an integer from 1-30, n, p and q are independently an integer from 1-20, t, u, v, w and x are independently integers from 1-1000, and J and Z are independently O or NR', wherein R' is hydrogen, substituted or unsubstituted alkyl, or substituted or unsubstituted aryl, wherein the weight average molecular weight of the polymer is greater than 1,000 Daltons.

15. The formulation of claim 14 wherein the arrangements of the units within the polymer are random.

16. The formulation of claim 1 comprising molecules to be delivered to a compartment of a cell, wherein the molecule is released at the pH of the compartment.

17. The formulation of claim 16 wherein the molecules and polyorthoester are precipitated together and formed into nanoparticles.

18. A method for delivering molecules to a compartment of a cell, wherein the molecule is released at the pH of the compartment, comprising
(i) providing a poly(amine-co-ester-co-ortho ester) or poly(amine-co-amides-co-orthoester) having the following formula:

Formula I

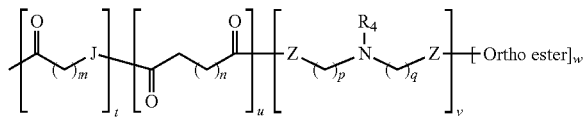

wherein each occurrence of m is an integer from 1-30, each occurrence of n, p, and q, is independently an integer from 1-20, each occurrence of t, u, v, and w is independently an integer from 1-1000, and J and Z are independently O or NR', wherein R' is hydrogen, substituted or unsubstituted alkyl, or substituted or unsubstituted aryl, wherein $R_4$ is hydrogen, alkyl, substituted alkyl, alkenyl, substituted alkenyl, alkynyl, substituted alkynyl, aryl, substituted aryl, heteroaryl, substituted heteroaryl, alkoxy, substituted alkoxy, aroxy, substituted aroxy, alkylthio, substituted alkylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group, wherein the ortho ester has the following formula:

Formula II

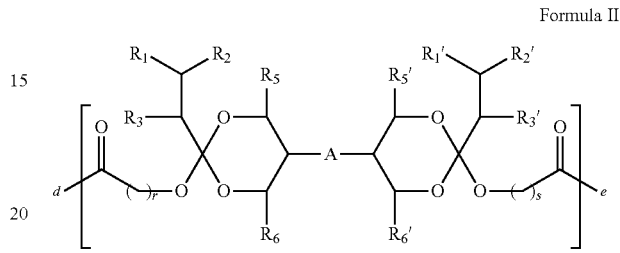

wherein r and s are independently an integer from 1-20, wherein A is absent or A is a single bond, wherein $R_1$, $R_1'$, $R_2$, $R_2'$, $R_3$, $R_3'$, $R_5$, $R_5'$, $R_6$ and $R_6'$ groups are independently hydrogen, alkyl, substituted alkyl, alkenyl, substituted alkenyl, alkynyl, substituted alkynyl, aryl, substituted aryl, heteroaryl, substituted heteroaryl, alkoxy, substituted alkoxy, aroxy, substituted aroxy, alkylthio, substituted alkylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly (ethylene glycol), peptide, or polypeptide group, wherein the ortho ester is attached to the rest of the polymer at points d and/or e, and wherein the arrangements of the units within the polymer are ordered or random, (ii) precipitating molecules to be delivered by mixing the orthoester polymer with the molecule in a solution, and (iii) forming the precipitate into nanoparticles.

19. The method of claim 18 comprising administering the nanoparticles in an effective amount to an individual or cells of an individual in need thereof.

20. The method of claim 18 wherein the nanoparticles are delivered to tissues having a low pH at which the nucleic acid is released.

21. The method of claim 18 wherein the tissues are cancerous, septic, poorly vascularized, infected, or necrotic.

22. A method of making a polymer, the method comprising, mixing an enzyme catalyst with monomer units under conditions to form a polymer having the formula:

Formula I

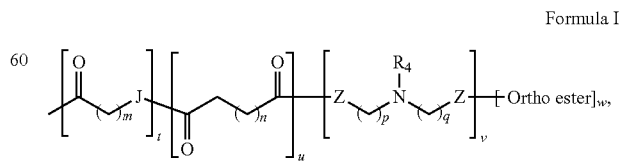

wherein the monomer units are selected from the group consisting of one or more lactones having the formula

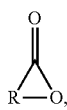

one or more diacids or diesters, having the formula

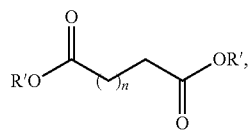

one or more an amine-diols, triamines, or hydroxy diamines, having the formula

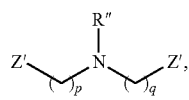

and one or more ortho esters having the formula:

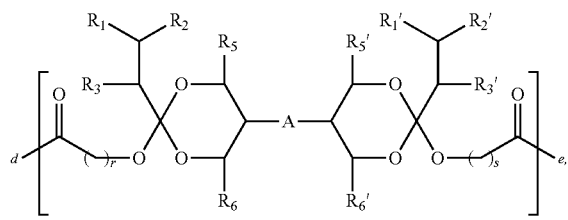

wherein R is $(CH_2)_m$;
wherein R' is hydrogen or alkyl;
wherein R" substituted or unsubstituted alkyl, or substituted or unsubstituted aryl;
wherein each Z' is independently OH or $N(R''')_2$, wherein R''' is hydrogen, substituted or unsubstituted alkyl, or substituted or unsubstituted aryl;

wherein m is an integer from 1-30;
each occurrence of n, p, and q are independently integers from 1-20;
x is an integer from 1 to 1000,
wherein r and s are independently an integer from 1-20,
wherein A is absent or A is a single bond,
wherein $R_1$, $R_1'$, $R_2$, $R_2'$, $R_3$, $R_3'$, $R_5$, $R_5'$, $R_6$, and $R_6'$ are independently hydrogen, alkyl, substituted alkyl, alkenyl, substituted alkenyl, alkynyl, substituted alkynyl, aryl, substituted aryl, heteroaryl, substituted heteroaryl, alkoxy, substituted alkoxy, aroxy, substituted aroxy, alkylthio, substituted alkylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group,
wherein the ortho ester is attached to the rest of the polymer at points d and/or e, and
wherein the arrangements of the units within the polymer are ordered or random.

23. The method of claim 22, wherein the enzyme catalyst is a lipase.

24. The method of claim 23, wherein the lipase is lipase B from *Candida antarctica*.

25. The method of claim 22, wherein the feed molar ratios of the ortho ester/diacid or diester/amine diol or triamine or hydroxy diamine/lactone is from about 10:90:100:10 to about 50:50:100:10.

26. The method of claim 22, wherein the weight average molecular weight of the polymers, as measured by gel permeation chromatography using narrow polydispersity polystyrene standards, greater than 1,000 Daltons.

27. The method of claim 22, comprising
(i) incubating the monomer units and enzyme catalyst at a temperature from between about 80° C. and about 90° C., at about 1 atm $N_2$.

28. The method of claim 27, further comprising, after step (i),
(ii) incubating the monomer units and enzyme catalyst at a temperature from between about 80° C. and about 90° C., at about 1.6 mm Hg.

* * * * *

SEQUENCE LISTING

```
<160> NUMBER OF SEQ ID NOS: 6

<210> SEQ ID NO 1
<211> LENGTH: 26
<212> TYPE: PRT
<213> ORGANISM: Artificial Sequence
<220> FEATURE:
<223> OTHER INFORMATION: Linker polypeptide

<400> SEQUENCE: 1

Glu Glu Glu Glu Glu Glu Glu Glu Glu Glu Glu Glu Glu Glu Glu Glu
1               5                   10                  15

Gly Gly Gly Gly Gly Gly Arg Gly Asp Lys
            20                  25

<210> SEQ ID NO 2
<211> LENGTH: 26
<212> TYPE: PRT
```

```
<213> ORGANISM: Artificial Sequence
<220> FEATURE:
<223> OTHER INFORMATION: Linker polypeptide

<400> SEQUENCE: 2

Arg Gly Asp Lys Gly Gly Gly Gly Gly Glu Glu Glu Glu Glu
1               5                   10                  15

Glu Glu Glu Glu Glu Glu Glu Glu Glu Glu
            20                  25

<210> SEQ ID NO 3
<211> LENGTH: 22
<212> TYPE: PRT
<213> ORGANISM: Artificial Sequence
<220> FEATURE:
<223> OTHER INFORMATION: Linker polypeptide

<400> SEQUENCE: 3

Gly Gly Gly Gly Gly Gly Glu Glu Glu Glu Glu Glu Glu Glu Glu
1               5                   10                  15

Glu Glu Glu Glu Glu Glu
            20

<210> SEQ ID NO 4
<211> LENGTH: 33
<212> TYPE: PRT
<213> ORGANISM: Artificial Sequence
<220> FEATURE:
<223> OTHER INFORMATION: Cell targeting peptide
<220> FEATURE:
<221> NAME/KEY: MISC_FEATURE
<222> LOCATION: (33)..(33)
<223> OTHER INFORMATION: Amide modification

<400> SEQUENCE: 4

Gly Asp Pro Asp Leu Gly Asp Val Asp Arg Gly Gly Gly Gly Gly
1               5                   10                  15

Gly Glu Glu Glu Glu Glu Glu Glu Glu Glu Glu Glu Glu Glu Glu
            20                  25                  30

Glu

<210> SEQ ID NO 5
<211> LENGTH: 11
<212> TYPE: PRT
<213> ORGANISM: Artificial Sequence
<220> FEATURE:
<223> OTHER INFORMATION: Cell targeting domain

<400> SEQUENCE: 5

Gly Asp Pro Asp Leu Gly Asp Val Asp Arg Gly
1               5                   10

<210> SEQ ID NO 6
<211> LENGTH: 5
<212> TYPE: PRT
<213> ORGANISM: Artificial Sequence
<220> FEATURE:
<223> OTHER INFORMATION: Cell targeting domain

<400> SEQUENCE: 6

Ala Ser Gly Pro Arg
1               5
```